(12) United States Patent
Holland

(10) Patent No.: US 7,197,404 B2
(45) Date of Patent: Mar. 27, 2007

(54) COMPUTATION OF RADIATING PARTICLE AND WAVE DISTRIBUTIONS USING A GENERALIZED DISCRETE FIELD CONSTRUCTED FROM REPRESENTATIVE RAY SETS

(76) Inventor: Richard Andrew Holland, 394 Beachley Hill Rd., Somerset, PA (US) 15501

( * ) Notice: Subject to any disclaimer, the term of this patent is extended or adjusted under 35 U.S.C. 154(b) by 312 days.

(21) Appl. No.: 10/790,404

(22) Filed: Mar. 1, 2004

(65) Prior Publication Data

US 2005/0192764 A1 Sep. 1, 2005

(51) Int. Cl.
| | |
|---|---|
| A61B 5/00 | (2006.01) |
| A61B 6/00 | (2006.01) |
| A61B 6/02 | (2006.01) |
| G06F 19/00 | (2006.01) |
| G01N 23/201 | (2006.01) |
| G01N 23/00 | (2006.01) |
| G01N 23/02 | (2006.01) |
| G21K 1/12 | (2006.01) |
| G01T 1/00 | (2006.01) |
| G01T 1/02 | (2006.01) |
| G01T 1/20 | (2006.01) |
| H05G 1/60 | (2006.01) |

(52) U.S. Cl. ............................ 702/28; 703/12; 378/13; 378/16; 378/18; 378/86; 250/363.01; 250/363.02; 250/363.04; 250/370.07; 600/310; 600/407; 600/473; 600/474; 600/1; 600/2; 600/477; 600/478

(58) Field of Classification Search .................. 702/28; 703/2; 600/310, 407, 473, 474, 475, 476, 600/477, 478, 1, 2; 378/86, 16, 18, 13, 11, 378/7; 250/363.01, 363.02, 363.03, 363.04, 250/370.07
See application file for complete search history.

(56) References Cited

U.S. PATENT DOCUMENTS

| | | | | |
|---|---|---|---|---|
| 6,029,079 A | * | 2/2000 | Cox et al. | 600/407 |
| 6,148,272 A | * | 11/2000 | Bergstrom et al. | 702/179 |
| 6,175,761 B1 | * | 1/2001 | Frandsen et al. | 600/436 |
| 6,301,329 B1 | * | 10/2001 | Surridge | 378/65 |
| 6,335,792 B1 | * | 1/2002 | Tsuchiya | 356/432 |
| 6,714,620 B2 | * | 3/2004 | Caflisch et al. | 378/65 |
| 2003/0144432 A1 | * | 7/2003 | Llinas et al. | 526/74 |
| 2003/0204126 A1 | * | 10/2003 | Rivard | 600/3 |

OTHER PUBLICATIONS

Scott et al. "Invariant Imbedding and the Calculation of Eigenvalues for Sturm-Liouville Systems" Computing, 1969, pp. 10-23.*

(Continued)

*Primary Examiner*—Kamini Shah
*Assistant Examiner*—Suzanne Lo
(74) *Attorney, Agent, or Firm*—McQuaide, Blasko, Fleming & Faulkner, Inc.

(57) ABSTRACT

The present system and method for simulating particles and waves is useful for calculations involving nuclear and full spectrum radiation transport, quantum particle transport, plasma transport and charged particle transport. The invention provides a mechanism for creating accurate invariants for embedding in general three-dimensional problems and describes means by which a series of simple single collision interaction finite elements can be extended to formulate a complex multi-collision finite element.

15 Claims, 15 Drawing Sheets

*Invention Process Block Diagram*

OTHER PUBLICATIONS

Bellman et al. "Random Walk, Scattering, and Invariant Imbedding I. One-Dimensional Discrete Case" Oct. 15, 1957 Proceedings of the National Academy of Sciences of the United States of America, vol. 43, No. 10, pp. 930-933.*

Bellman et al. "Dissipation Functions and Invariant Imbedding" Aug. 15, 1960, Proceedings of the National Academy of Sciences of the United States of America, vol. 46, No. 8, pp. 1145-1147.*

Bellman et al. "Invariant Imbedding and the Reduction of Two-Point Boundary Value Problems to Initial Value Problems" Oct. 25, 1960, pp. 1646-1649.*

E. Cashwell & C. Everett, The Practical Manual on the Monte Carlo Method for Random Walk Problems, Pergamon Press (1959). (out of print).

Analytic Reductions for Transmission and Leakage Probabilities in Finite Tubes and Hexahedra, 104 Nucl. Sci. & Eng., 209-216 (1990).

A Transport Method for Treating Three Dimensional Lattices of Heterogeneous Cells, 101 Nucl. Sci. & Eng., 217-225 (1989).

J. Karkkainen & E. Ukkonen, Two- and Higher-Dimensional Pattern Matching in Optimal Expected Time, 29 SIAM J. Comput., 571-589 (1999).

R. Belman, G.M. Wing, An Introduction to Invariant Imbedding, R. Belman, SIAM (1992) ISBN 0-89871-304-8.

A. Shimizu, Development of Angular Elgenvalue Method for Radiation Transport Problems, 37 J. Nuclear Science and Technology, 15-25 (2000).

Olvey et al., Accuracy Comparisons for Variational R, T and T-1 Response Matrix Formulations, 14 Annals of Nuclear Energy, 203-209 (1987).

Sternick et al., The Theory & Practice of Intensity Modulated Radiation Therapy, Advanced Medical Publishing, 37-49 (1997).

Y. Nievergelt, Wavelets Made Easy, Birkhauser (1999) ISBN 0-8176-4061.

P.R. Bevington, Data Reduction and Error Analysis for the Physical Sciences, p. 153, McGraw Hill Book Company, (1969) Library of Congress Catalogue No. 69-16942.

R.D. Lawrence and J.J. Dorning, A Nodal Green's Function Method for Multidimensional Diffusion Calculations, Nuclear Science and Engineering 76, 218-231 (1980).

F.C. Lockwood and N.G. Shah, A New Radiation Solution Method for Incorporation in General Combustion Prediction Procedures, Imperial College of Science and Technology, London, 1981.

K. Kobayashi, et al. 3D Radiation Transport Benchmark Problems and Results for Simple Geometries with Void Region. Progress in Nuclear Engineering, vol. 39, No. 2, pp. 119-144, 2001.

* cited by examiner

Real Single Particle Passing Thru Finite Surface ΔS

Small Grid System of Voxels

*Subset of Rays Traversing 2D Grid System from Reference Surface*

*Rays within a particular Ray Set $\Delta\Re$ from a Reference $\Delta S$ Occupying Solid Angle Group $\Delta\Omega$ Traversing Voxels*

*An LVG From A Reference Voxel Surface 2D or Overhead View*

*Pointer/Transport Multiplier Memory Device*

Fig.7 Invention Process Block Diagram

*Pre-Computed Ray Set Geometric Properties
(Figure 7, Block 2AI Embodiment)*

```
 1  12927 [ 0][ 0][ 0] -  10
 2  [0][0][0]-336-:336-|0,4:1,2:37,2:73,2:109,4:110,2:146,2:182,1:188,4:189,2:
 3  336
 4  336
 5  7.850558564946638e-05  6.784620633418995e+00  6.623391839641562e+00  2.819600000000000e-06
 6  - [ 0][ 0][ 0] - 4 - 1.019279586938127e+00
 7  - [ 0][ 0][ 1] - 2 - 9.413711183984186e-02
 8  - [ 1][ 0][ 1] - 2 - 1.113416698777977e+00
 9  - [ 2][ 0][ 1] - 2 - 1.113416698777977e+00
10  - [ 3][ 0][ 1] - 4 - 8.578329108772469e-02
11  - [ 3][ 0][ 2] - 2 - 1.027633407690246e+00
12  - [ 4][ 0][ 2] - 2 - 1.113416698777977e+00
13  - [ 5][ 0][ 2] - 1 - 1.205002778411613e-01
14  - [ 5][ 1][ 2] - 4 - 1.452034161741309e-01
15  - [ 5][ 1][ 3] - 2 - 8.477130047626756e-01
16  3 detail
17 0 6.659682137068683e+00  6.677133394014817e+00  6.623885099075124e+00
18     5.176445578231292e-01 - 6.677134770900707e+00
19         9.869710645786067e-01
20         1.229759582661787e-01
21         1.109947022844781e+00
22         1.109947022844781e+00
23         9.590364158782305e-02
24         1.014043381256952e+00
25         1.109947022844781e+00
26         1.418524854996891e-01
27         1.729307559421361e-01
28         7.951637814029552e-01
29  1 6.697852583372446e+00  6.730875835863125e+00  6.677135463944154e+00
30     4.295457766439909e-01 - 6.730877702159851e+00
31         1.049588508542006e+00
32         6.672025535341053e-02
33         1.116308763895405e+00
34         1.116308763895405e+00
35         8.023541120737232e-02
36         1.036073352688041e+00
37         1.116308763895405e+00
38         1.034249093947345e-01
39         1.237661683734199e-01
40         8.891176861272597e-01
41  2 6.743640693621075e+00  6.780941997558494e+00  6.730879046744218e+00
42     5.280966553287982e-02 - 6.784620633418995e+00
43         1.094353538739710e+00
44         2.958657686380297e-02
45         1.123940115603512e+00
46         1.123940115603512e+00
47         3.584565699482696e-02
48         1.088094458608688e+00
49         1.123940115603512e+00
50         4.868157770248906e-02
51         5.259631315096771e-02
52         1.022662224750057e+00
```

*Sample Prototype Code Output Fragment from Figure 8 Pre-Computational Process*

*Fig. 9*

*Pre-Compute Input LVG Construction Process (Figure 7, Block 2A Embodiment)*

*Inline Ray Set Based LVG Discrete Particle Transport Multipliers*
*(Figure 7, Block 2 Embodiment)*

Sample Interaction Model for Radiation
(Figure 7, Block 5 Non-Fissile Embodiment)

Sample Problem

Key

| |
|---|
| Monte Carlo |
| Present Invention |
| % Difference |

Plane 4 Total Sum

| |
|---|
| 7.2516E-03 |
| 7.2366E-03 |
| 0.21% |

| | | | | |
|---|---|---|---|---|
| 8.3684E-04 | 6.8796E-04 | 5.8915E-04 | 4.6043E-04 | 8.4336E-05 |
| 8.4715E-04 | 6.9370E-04 | 5.9632E-04 | 4.5825E-04 | 8.3562E-05 |
| -1.23% | -0.83% | -1.22% | 0.47% | 0.92% |
| 6.8319E-04 | 5.6220E-04 | 4.9065E-04 | 3.9478E-04 | 7.4409E-05 |
| 6.8121E-04 | 5.6004E-04 | 4.9042E-04 | 3.8819E-04 | 7.2760E-05 |
| 0.29% | 0.38% | 0.05% | 1.67% | 2.22% |
| 3.8524E-04 | 3.1986E-04 | 2.9711E-04 | 2.6043E-04 | 5.2384E-05 |
| 3.8161E-04 | 3.1720E-04 | 2.9424E-04 | 2.5564E-04 | 5.1326E-05 |
| 0.94% | 0.83% | 0.96% | 1.84% | 2.02% |
| 1.5681E-04 | 1.3441E-04 | 1.3593E-04 | 1.4031E-04 | 3.2430E-05 |
| 1.5629E-04 | 1.3213E-04 | 1.3582E-04 | 1.3794E-04 | 3.1472E-05 |
| 0.33% | 1.69% | 0.08% | 1.69% | 2.95% |
| 4.8680E-05 | 4.8330E-05 | 5.9359E-05 | 7.7734E-05 | 2.8368E-05 |
| 4.9014E-05 | 4.8612E-05 | 6.0540E-05 | 7.7144E-05 | 2.8356E-05 |
| -0.69% | -0.58% | -1.99% | 0.76% | 0.04% |
| 1.4523E-05 | 2.3141E-05 | 4.2318E-05 | 6.4404E-05 | 3.4570E-05 |
| 1.4176E-05 | 2.2726E-05 | 4.2186E-05 | 6.2589E-05 | 3.4150E-05 |
| 2.39% | 1.80% | 0.31% | 2.82% | 1.22% |

*Plane 4*
*Planer Interaction Rate Results*

*Fig. 14*

| Case | Distance | Monte Carlo (GMVP) Base Case | | Present Invention | | | TORTE With FNSUNCL3 | | | ARDRA P21 Solution | | | EVENT P9 Solution | | |
|---|---|---|---|---|---|---|---|---|---|---|---|---|---|---|---|
| | (cm) x, y, z | Point Flux cm$^{-2}$ s$^{-1}$ | FSD σ(%) | Node Avg. Flux cm$^{-2}$ s$^{-1}$ | | Absolute % Error | Point Flux cm$^{-2}$ s$^{-1}$ | | Absolute % Error | Point Flux cm$^{-2}$ s$^{-1}$ | | Absolute % Error | Point Flux cm$^{-2}$ s$^{-1}$ | | Absolute % Error |
| 1Ai | 5, 5, 5 | 5.9566E+00 | 0.000 | 6.0400E+00 | | 1.40% | 5.9216E+00 | | 0.59% | 5.7700E+00 | | 3.13% | 5.9670E+00 | | 0.17% |
| | 15, 5, 5 | 1.3719E+00 | 0.000 | 1.3560E+00 | | 1.16% | 1.3062E+00 | | 4.79% | 1.6300E+00 | | 18.82% | - | | - |
| | 25, 5, 5 | 5.0087E-01 | 0.000 | 5.0290E-01 | | 0.41% | 4.8947E-01 | | 2.28% | 4.4600E-01 | | 10.96% | - | | - |
| | 35, 5, 5 | 2.5243E-01 | 0.000 | 2.5460E-01 | | 0.86% | 2.4824E-01 | | 1.66% | 2.9200E-01 | | 15.68% | - | | - |
| | 45, 5, 5 | 1.5026E-01 | 0.000 | 1.5060E-01 | | 0.23% | 1.4818E-01 | | 1.38% | 1.6000E-01 | | 6.48% | - | | - |
| | 55, 5, 5 | 5.9529E-02 | 0.000 | 5.8166E-02 | | 2.29% | 5.8810E-02 | | 1.21% | 6.6900E-02 | | 12.38% | 7.0861E-02 | | 19.04% |
| | 65, 5, 5 | 1.5328E-02 | 0.000 | 1.5283E-02 | | 0.30% | 1.5165E-02 | | 1.07% | 1.7100E-02 | | 11.56% | 1.8687E-02 | | 21.91% |
| | 75, 5, 5 | 4.1769E-03 | 0.000 | 4.2170E-03 | | 0.96% | 4.1358E-03 | | 0.98% | 3.3300E-03 | | 20.28% | 5.0464E-03 | | 20.82% |
| | 85, 5, 5 | 1.1853E-03 | 0.000 | 1.2186E-03 | | 2.81% | 1.1743E-03 | | 0.93% | 7.4400E-04 | | 37.23% | 1.3882E-03 | | 17.11% |
| | 95, 5, 5 | 3.4685E-04 | 0.000 | 3.2850E-04 | | 5.29% | 3.4377E-04 | | 0.89% | 3.2200E-04 | | 7.16% | 3.8732E-04 | | 11.67% |
| 1Aii | 5, 5, 5 | 8.2926E+00 | 0.021 | 8.290E+00 | | 0.03% | 8.2597E+00 | | 0.40% | 7.9400E+00 | | 4.25% | 8.2595E+00 | | 0.40% |
| | 15, 5, 5 | 1.8703E+00 | 0.005 | 1.827E+00 | | 2.31% | 1.8345E+00 | | 1.91% | 2.1800E+00 | | 16.56% | - | | - |
| | 25, 5, 5 | 7.1398E-01 | 0.003 | 7.051E-01 | | 1.24% | 7.1045E-01 | | 0.49% | 6.4500E-01 | | 9.66% | - | | - |
| | 35, 5, 5 | 3.8469E-01 | 0.004 | 3.692E-01 | | 4.03% | 3.6632E-01 | | 4.77% | 4.3000E-01 | | 11.78% | - | | - |
| | 45, 5, 5 | 2.5398E-01 | 0.006 | 2.485E-01 | | 2.16% | 2.3171E-01 | | 8.77% | 2.6200E-01 | | 3.16% | - | | - |
| | 55, 5, 5 | 1.3722E-01 | 0.073 | 1.304E-01 | | 4.97% | 1.3236E-01 | | 3.54% | 1.4600E-01 | | 6.40% | 1.5426E-01 | | 12.42% |
| | 65, 5, 5 | 4.6591E-02 | 0.117 | 4.611E-02 | | 1.03% | 4.7617E-02 | | 2.20% | 4.8400E-02 | | 3.88% | 5.3594E-02 | | 15.03% |
| | 75, 5, 5 | 1.5877E-02 | 0.197 | 1.604E-02 | | 1.03% | 1.6049E-02 | | 1.09% | 1.5400E-02 | | 3.00% | 1.8164E-02 | | 14.41% |
| | 85, 5, 5 | 5.4704E-03 | 0.343 | 5.496E-03 | | 0.47% | 5.2495E-03 | | 4.04% | 5.0800E-03 | | 7.14% | 6.1428E-03 | | 12.29% |
| | 95, 5, 5 | 1.8508E-03 | 0.619 | 1.903E-03 | | 2.80% | 1.6929E-03 | | 8.53% | 1.2400E-03 | | 33.00% | 2.0208E-03 | | 9.19% |

*Kobayashi International 3D Benchmark Problem 1A Comparison*

*Fig.15*

| Case | Distance | Monte Carlo (GMVP) Base Case | | Present Invention No Surface Cut | | | Present Invention 2x2 Surface Cut | | | Present Invention 2x2 6th Order Coeff. | | |
|---|---|---|---|---|---|---|---|---|---|---|---|---|
| | | Point Flux | FSD | Node Avg. Flux | Absolute | | Point Flux | Absolute | | Point Flux | Absolute | |
| | (cm) | cm⁻²s⁻¹ | σ(%) | cm⁻²s⁻¹ | %Error | | cm⁻²s⁻¹ | %Error | | cm⁻²s⁻¹ | %Error | |
| | x,y,z | | | | | | | | | | | |
| 1Ai | 5,5,5 | 5.9566E+00 | 0.000 | 6.0645E+00 | 1.81% | | | | | | | |
| | 15,5,5 | 1.3719E+00 | 0.000 | 1.3911E+00 | 1.40% | | | | | | | |
| | 25,5,5 | 5.0087E-01 | 0.000 | 5.0110E-01 | 0.05% | | | | | | | |
| | 35,5,5 | 2.5243E-01 | 0.000 | 2.5332E-01 | 3.53% | | | | | | | |
| | 45,5,5 | 1.5026E-01 | 0.000 | 1.4900E-01 | 0.84% | | | | | | | |
| | 55,5,5 | 5.9529E-02 | 0.000 | 5.8632E-02 | 1.51% | | 5.9734E-02 | 0.34% | | 6.5482E-02 | 10.00% | |
| | 65,5,5 | 1.5328E-02 | 0.000 | 1.5302E-02 | 0.17% | | 1.4735E-02 | 3.87% | | 1.5542E-02 | 1.40% | |
| | 75,5,5 | 4.1769E-03 | 0.000 | 4.2007E-03 | 0.57% | | 4.0044E-03 | 4.13% | | 4.1066E-03 | 1.68% | |
| | 85,5,5 | 1.1853E-03 | 0.000 | 1.2104E-03 | 2.12% | | 1.0669E-03 | 9.99% | | 1.0993E-03 | 7.26% | |
| | 95,5,5 | 3.4685E-04 | 0.000 | 3.3002E-04 | 4.85% | | 3.4674E-04 | 0.03% | | 3.4294E-04 | 1.13% | |

*Problem 1Ai No Scatter Surface Cut at x=50 cm*

*Fig.16*

| Problem/Method | Machine | Process Time (sec) |
|---|---|---|
| Present Invention 1Ai | Pentium Xeon 2.2 GHz 32 bit | 236 Setup 0.01 Exec |
| Present Invention 1Ai Cut | Pentium Xeon 2.2 GHz 32 bit | 163 / 0.021 |
| Present Invention 1Ai Coeff | Pentium Xeon 2.2 GHz 32 bit | 120/ 1.798 |
| Present Invention 1Aii | Pentium Xeon 2.2 GHz 32 bit | 4996 / 33.34 |
| TORT FNSUNCL3 1Ai | FUJITSU AP3000/24 - 296 MHz | 9944 |
| TORT FNSUNCL3 1Aii | FUJITSU AP3000/24 - 296 MHz | 12781 |
| GMVP Base 1Ai | FUJITSU VPP500 100MHz | 1440 |
| GMVP Base 1Aii | FUJITSU VPP500 100MHz | 378,000 |
| ARDRA 1Ai | IBM ASCI Blue-Pacific | 7847 |
| ARDRA 1Aii | IBM ASCI Blue-Pacific | 10223 |
| EVENT 1Ai | AXP1000 667 MHz Alpha | 6344 |
| EVENT 1Aii | AXP1000 667 MHz Alpha | 8357 |

*Time Comparison of Present Invention Problem 1Ai and 1Aii*

*Fig.17*

COMPUTATION OF RADIATING PARTICLE AND WAVE DISTRIBUTIONS USING A GENERALIZED DISCRETE FIELD CONSTRUCTED FROM REPRESENTATIVE RAY SETS

FIELD OF THE INVENTION

The present invention relates to a process for simulating the transportation of particles and/or waves propagating through a medium. More specifically, the instant invention relates to the process of utilizing computational algorithms and methodologies to simulate both nuclear and electromagnetic radiation transmitting and interacting within a particular medium.

DESCRIPTION OF THE PRIOR ART

While the instant invention has many different applications and addresses numerous problems in the prior art, medical applications offer the best context within which to describe the invention and the manner in which it overcomes prior art. For over a century, physicians have been administering ionizing radiation to patients for the purpose of treating various types of cancerous tumors. Throughout this time, many advances have been made within the Radiation Oncology field. One particular technological advance has been the practice of modulating the intensity of the radiation prior to exposing the patient. Upon modulating the radiation, the beam becomes non-uniform and the dose distribution profile is irregular. The irregular dose distribution is advantageous in that, the maximum dose or intensity of the beam can be precisely positioned within and confined to the target volume of the tumor while simultaneously minimizing the dose or intensity of the beam to healthy tissue surrounding the tumor.

Presently, such practice is often referred to as Intensity Modulated Radiation Therapy, hereinafter referred to as IMRT. Modulating the intensity of the beam is a conventional practice and has been used in the field of Radiation Oncology for decades. More recently, the use Multileaf Collimators (MLC) to modulate beam intensities has become popular since MLC have the dual capability of performing Three Dimensional Conformal Radiation Therapy (3DCRT) and IMRT.

However, due to the complexity of intensity modulated beams and/or their irregular field shapes produced by the MLC, determining depth dose distributions within the patients is extremely difficult, if not impossible through manual calculations. As such, the employment of computational algorithms is required. Through the use of computers, ionizing radiation propagating through and interacting with a material can be simulated through algorithms. Therefore, such computational algorithms can provide the necessary depth dose distributions without laborious manual calculations.

For many years, Monte Carlo or stochastic methods have been used to determine particle transport in three dimensions. Such computational methodologies for particle and wave simulations are used in a number of applications. For instance, in Intensity Modulated Radiation Therapy three-dimensional treatment planning, Monte Carlo calculations are employed, as well as semi-empirical methods based on a conventional ray-buildup factor technique. Additionally, fast Fourier transforms are recurrently used with superposition to compute scattered dose throughout the tissue phantom. In the nuclear engineering field, $\alpha$, $\beta$ and $\gamma$ neutron and proton radiation is simulated in nuclear transport calculations for applications ranging from nuclear reactor core design to shielding to nuclear medicine. In addition, numerous equipment designs, ranging from radiation detectors to microwave ovens, also profit from transport computations.

Radiative heat transfer, useful for combustor and boiler design, is another area in which computational methods have been used. For instance, in the "discrete transfer method" representative rays between bounded reflecting surfaces are used to model thermal radiation traversing a grid system of control volumes. Diverse integration kernels are applied to specific lengths associated with these rays to determine the intensity of beams passing through the system. The intensity of representative rays is computed on entrance and exit to control volumes with rays reflecting off of fixed problem boundaries.

The "Invariant Imbedding" technique involves imbedding invariant solutions within a large framework and coupling finite element solutions and nodal computations. This technique, however, retains functional particle density continuity concepts that are relatively inaccurate for extension beyond one-dimension (although using the discrete transfer method to determine finite element imbedding invariants provides a practical means of extending ray solutions to far larger problems).

While the existing methods are adequate for many computational applications, they possess a number of shortcomings. One significant shortcoming is their failure to provide mechanisms for reducing an extremely large set of rays to simple scalar multipliers that can be used to compute radiation distributions from distributed sources in a generalized field. Another disadvantage is that the known methodologies do not describe how a local system of representative rays can be extended from one set of control volumes to another set. The methods of the prior art also fail to include mechanisms for creating invariant voxel groups that can be imbedded in larger systems using a generalized field. A further shortcoming of the existing methodologies is that they fail to provide means by which a series of simple single collision interaction finite elements can be extended to formulate a complex multi-collision finite element. Finally, the methods of the prior art lack a generalized scheme for all forms of radiating particles (ranging from electromagnetic radiation to quantum particles and from neutrons to sound waves). Accordingly, there is a need for a computational methodology that overcomes the shortcomings of the prior art.

Thus, on account of the foregoing shortcomings, while prior art computational methods are capable of providing solutions to transport simulations, they are unable to simulate particle transport with both acceptable speed and accuracy. Typical methods such as Monte Carlo, can, under certain conditions, produce a simulation with sufficient accuracy, but they fail to perform the simulation within a reasonable amount of time to be used within a Radiation Oncology clinic and can be too exotic, expensive and time consuming for other applications, such as electronic device design. Alternatively, other simulations possess the needed speed, but in doing so sacrifice essential accuracy. As such, there is a critical need in the art to provide a radiation transport simulation computer methodology capable of achieving acceptable simulation speed and accuracy.

SUMMARY OF THE INVENTION

The present invention is a system and computational methodology for simulating particles and waves. The invention is particularly useful for calculations involving nuclear and full spectrum (radio to gamma ray) electromagnetic radiation transport as well as quantum particle transport, plasma transport and charged particle transport. The invention is also useful for vibrational/sound wave computations and radiative heat transfer.

The present invention represents a significant conceptual departure from the prior art in that functional representations of particle densities have been dropped in favor of a discrete particle value within a discrete finite element solved using direct methods. The instant invention advantageously provides a mechanism for creating accurate invariants [See R. Belman, G. M. Wing, *An Introduction to Invariant Imbedding*, R. Belman, SIAM (1992) ISBN 0-89871-304-8] for embedding in general three-dimensional ("3D") problems and describes means by which a series of simple single collision interaction finite elements can be extended to formulate a complex multi-collision finite element.

Results show that the invention described herein is at least ten (10), and as much as one thousand (1000) times or more faster than the computational methods of the prior art. Results also show significant improvement over direct method, ray effect intensive mitigation benchmark problems. The foregoing results were obtained using a digital computer. However, the present invention also contemplates the use of analogue and digital-analogue hybrids for specialty—fast computation of particle transport. For instance, the invention can be used with a fast analogue control system in Intensity Modulated Radiation Therapy three-dimensional treatment planning to provide real-time computation of particle transport for use on external beam machines in conjunction with patient position data.

As stated above, the examples provided herein are primarily described in terms of a computational device for calculating radiation distribution for medical applications. Specifically referenced are examples regarding Intensity Modulated Radiation Therapy three-dimensional treatment planning (hereinafter "IMRT 3DRTP") for computation of gamma and x-ray particle transport in human tissue used for cancer radiotherapy. However, the examples also demonstrate the application of the invention in the other fields. These fields, include but are not limited to the following: medical radiation treatment planning simulation, electronic device design (e.g. microwave ovens and computer chips), RADAR (for electromagnetic radiation modeling), SONAR (for sound wave simulation), electrical transmission device design, optics, radiative heat transfer, nuclear shielding and reactor simulation, astrophysics, boiler and combustion simulation, telecommunications (e.g. to determine the optimal placement of cell phone towers), and mechanics. The adaptability of the invention is due, in part, to its unique algorithmic machinery, which is capable of modeling various applications through the use of replaceable (referring to a function pointer in C, or an object oriented computer language) integration kernels and interaction models. Defined Below, Integration Kernels used within FIG. 10 B.5, FIG. 11 B.3 and FIG. 12 B.3. Interaction Model explicitly shown in FIG. 7 Block 5.

DEFINITIONS

The following terms are prescribed definitions to aid and facilitate in the understanding of the present invention and such terms are not intended to be repugnant to their conventional meaning within the field of the invention.

Particle—A particle is defined as a packet of energy being of dual nature, in that the packet of energy can be a discrete finite object or a wave having a particular wavelength or frequency. This concept of the dual state of energy is not novel, but has been conventionally accepted within the general scientific field.

Examples of particles conforming to this definition include but are not limited to electromagnetic radiation such as $\gamma$-rays, x-rays, as well as other nuclear particles such as neutrons, alpha particles, protons and electrons. $\Delta x$—Bold $\Delta x$ represents a finite interval from x to x+$\Delta x$ of the variable x.

In reference to surfaces, $\Delta s$ represents a discrete surface plane of finite area (not the linear measure associated with an arc). Note that this bold notation for $\Delta x$ refers to the present invention, while the un-highlighted $\Delta x$ refers to the classical mathematic increment.

Discrete Particle—As a key component of the instant invention, a discrete particle is a real number tally in which a number of particles are represented within discrete finite state variables (i.e. a discrete phase space).

Within IMRT 3DRTP, a discrete particle is defined as P[$\Delta s$, $\Delta \Omega$, $\Delta t$], wherein P is the number of particles associated with a surface plane of finite area $\Delta s$, traversing within solid angle set $\Delta \Omega$ and within finite interval of time $\Delta t$. However as a mathematical device it is not at a point, but rather a constant value across a finite interval.

Although the foregoing discrete particle state variables $\Delta s$, $\Delta \Omega$ and $\Delta t$, are the preferred state variables for simulating Radiation Transport for IMRT 3DRTP, the instant invention is not limited to only these variables. Various other state variables include, but are not limited to, discrete energy groups, charge, quantum spin, or ray sets (defined below).

Voxel—A voxel can be thought of as the volume form of a pixel wherein a pixel is pertinent to an image within a two dimensional plane, a voxel is associated with a three dimensional image of an object. Each voxel represents both the spatial surfaces and the bounded homogenized material composition disposed therein. Although it is less difficult to visualize a regular shape as a voxel, such as a cube with six (6) surface sides, voxels need not be of uniform shape. As an example, in 3DRTP IMRT, Voxels may be shaped as parts of bones and may encompass one or several sections of an organ. The term voxel is common to prior art descriptions of IMRT computer solutions.

Grid—A grid, in the instant invention, is considered to be a finite system of adjacent voxels with a number of surfaces on each voxel. A simple conceptual example would be a $3^3$ set of voxels forming a cube, wherein each voxel has six surface faces. A grid system is used to represent a physical system of material in three-dimensional space. It should be emphasized that voxels and grids may be regular or irregular in shape. For instance, in 3DRTP IMRT an irregular grid system of voxels is shaped to match critical regions including, but not limited to, organs and bones.

Ray Set—A ray set is a number of representative rays from 1 to n, where n is a finite integer. These rays represent the average relative fraction and voxel path length of all rays emanating from a surface or volume, and traversing a grid. Each ray within a ray set has a unique fraction and unique voxel path length. However the ray traverses the same pathway through the voxel grid as other members of its set.

A ray set is distinguishable from a beamlet in that a ray set represents the geometric pathways over which radiation traverses while a beamlet is an actual beam of radiation emanating from a source with a specific energy spectrum. Ray sets are used throughout the phantom/problem media to couple all locations within a phantom/problem, whereas beamlets are typically external to a phantom and project towards a phantom from a fixed point.

Local Voxel Group—A Local Voxel Group (LVG) is a subset of grids or collection or grouping of voxels referenced from a particular voxel surface or volume. From this voxel surface or volume, ray sets emanate through local voxels and extend to the outer surface of the local voxel group. The referenced voxel surface is important because local voxel groups overlap and are not fixed finite elements except in reference to a particular surface.

Interaction Model—Interaction Model (IM) refers to the methodology applied in computing the distribution of particles once they are tallied as colliding with intervening material within voxels. An Interaction Model is required to model particle interaction, reflection or scatter and state change. Interaction Modules determine discrete particle distribution emanating from a voxel surface by considering all relevant material and state variables. Interaction Modules also determine particle distributions for ray sets within discrete solid angle groups $\Delta\Omega$.

Interaction Tallies—Closely related to the concept of an Interaction Model is concept of the interaction tally. The interaction tally may be as simple as a singular homogenous count of interactions that occurs within voxel volumes, to a sophisticated tally that embodies particle entrance state values such as $\Delta s$, $\Delta E$, $\Delta\Omega$, $\Delta t$ and $\Delta\Re$ or other state variables including, but not limited to quantum spin (quantum mechanics), force (mechanical applications) or temperature (radiative heat transfer). Interaction tallies may also apply to function coefficients. For example, the instant invention may be used to directly populate function coefficients associated with surface or spherical harmonic representation of angular particle distributions.

Homogenized—This term refers to volumetric averaged or interaction averaged material properties used in particle transport calculations.

Integration Kernels—For particle transport, integration kernels refer to the straight-line un-collided intensity kernel associated with particles. For most forms of radiating particles, the appropriate integration kernel is simply $e^{-\Sigma\Delta r}$, where $\Sigma$ is the total macroscopic cross-section for particle-material interaction and $\Delta r$ is the distance traversed within a particular voxel. This represents the un-collided transmitted particle, while $1-e^{-\Sigma\Delta r}$ represents the interacting component. In instances where the interaction model assumes modified $P_1$ isotropic scatter, $\Sigma$ represents the transport cross section as opposed to the total cross section.

Transport Multipliers—This term refers to a numerical value as described in FIGS. 6 and 10 representing the final summation of the uncollided fraction of discrete particles transported from a source location (surface or volume) to a terminal location (surface, volume, or function coefficient).

Terminal—Terminal refers to a position or function coefficient where a particle or fraction of attenuated particles end are accumulated. There can be multiple terminals per voxel and surface. A pointer may point to a terminal multiplier or a plurality of multipliers associated with several terminals.

Terminal Surface—A Terminal Surface is the surface bounding a Local Voxel Group upon which particles are tallied.

Substantial Convergence—A value that sufficiently approaches the mathematically idealized convergence value.

BRIEF DESCRIPTION OF THE DRAWINGS

FIG. 9 represents a simulated output for a particular ray set obtained by utilizing the block body diagram steps set forth in FIG. 8 of the present invention.

FIG. 11 depicts processes and/or object blocks.

FIG. 14 depicts simulated radiation transport outputs for both the instant invention and a prior art technique. Although the accuracy of both systems are comparable, the instant invention computes the simulation nearly 1000 times faster.

FIG. 15 presents simulated radiation transport result comparisons for problem 1A of an international standard benchmark set "3D Radiation Transport Benchmark Problems and Results for Simple Geometries with Void Region", ISSN 0149-1970 "Progress in Nuclear Energy". The results compare the present invention with other respected computer codes showing the accuracy improvement of the present invention.

FIG. 16 shows a comparison of problem 1A results with a cut surface illustrating the present invention's ability to accurately predict results behind a tally deposition surface. This illustrates the present invention's ability to simulate embedded problems.

FIG. 17 presents a time and machine comparison for solution of problems 1A results as shown in FIGS. 15 and 16. These time comparisons illustrate the 1000 fold speed advantage of the instant invention.

DETAILED DESCRIPTION OF THE INVENTION

Monte Carlo tracks each discrete particle history exactly and develops a stochastic result using hundreds of millions (if not billions) of exact particle histories (E. Cashwell & C.

Everett, *The Practical Manual on the Monte Carlo Method for Random Walk Problems*, Pergamon Press (1959)). The present invention inverts this process by defining discrete particles that occupy computer memory in a detailed phase space—essentially representing millions of distinct phase space particle count values. Stated otherwise, the present invention exactly and efficiently computes distributed phase space discrete particle transport to local surfaces, function coefficients and volumes, reducing the results of these calculations to a multiplication field appropriate for each surface, function coefficient and volume. The approximation involved in the calculation is the assumption that the increment of the discrete particle itself is truly constant. Thereafter, "exact" calculations are used to determine generalized field transport multipliers in a local area to create continuity, with extensions to a generalized area.

Discrete particles emanating from surfaces and volumes are directly "wired" to LVG neighboring surfaces, function coefficients and volumes through multiplier, voxel pointer pairs—to provide a near exact local solution of particle transport (the assumption being the constancy of the discrete particle itself). The LVG provides a local exact solution that reduces the particle count contribution from a local reference voxel volume or surface to external voxel volumes and surfaces. This provides the accuracy required to tackle three-dimensional problems, as opposed to imbedded invariants methods that break down past one dimension. The LVG multiplier field greatly reduces ray effects as particles are properly distributed in a local system. Those particles that are not distributed within the LVG are attenuated and emanate from the LVG surface. The distribution of particles emanating from a surface may be explicitly tracked either through a direct tally process or function deposition in a least squares sense to determine the angular distribution at the surface interface. In a similar fashion, function coefficient tallies may be used with complex interaction models to allow for high order particle scattering, for example anisotropic $P_5$.

Figure 7:
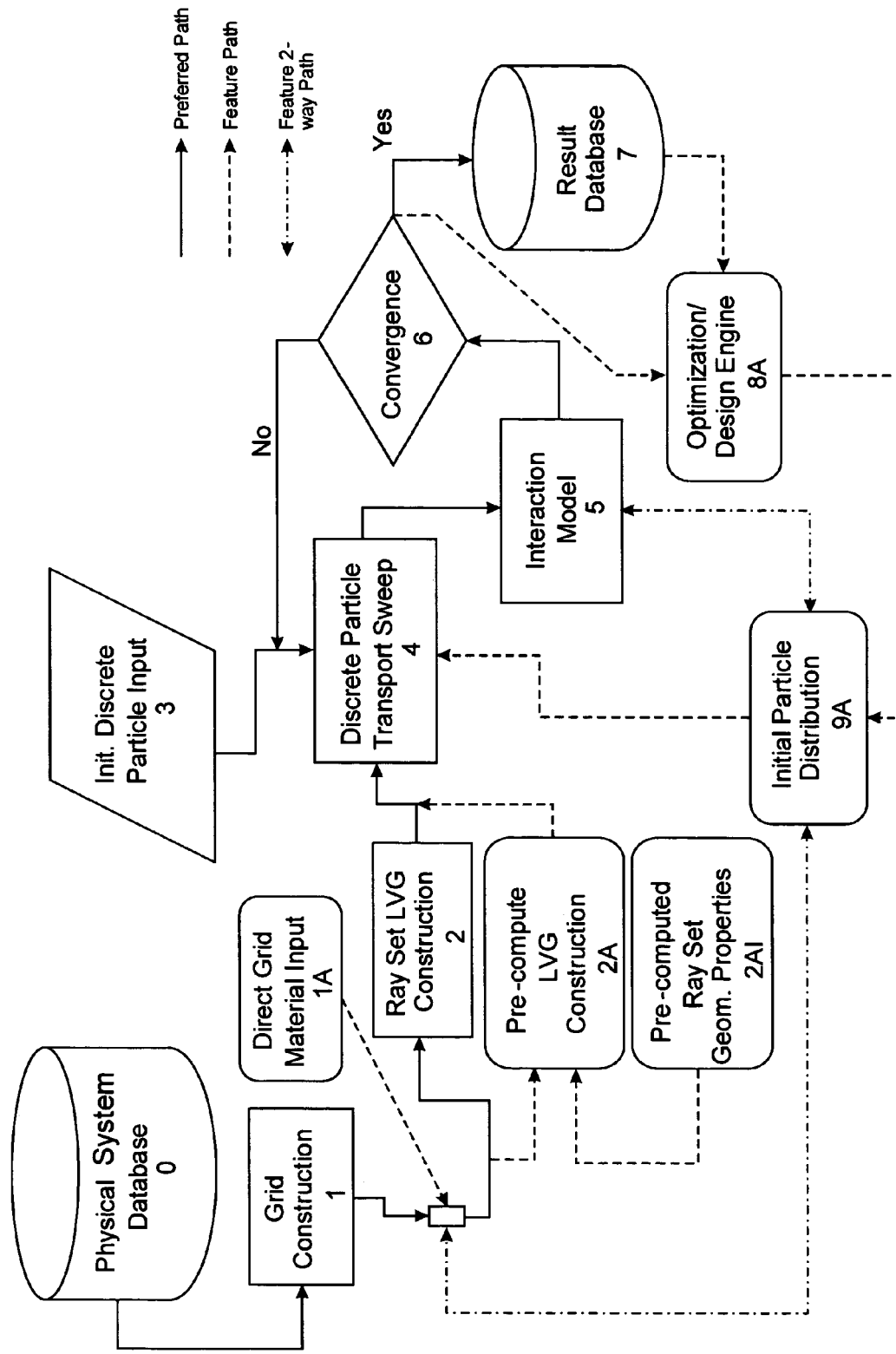
FIG. 7 represents a preferred embodiment of the instant invention with preferred logical process pathways and alternative paths in a block body diagram format. Each block within the figure represents a step or a computer software directive in the process of simulating the transport of particles through a medium.

A ray set concept is introduced to the phase space of the discrete particles to provide accurate LVG-to-LVG surface interface transport of particles, further improving accuracy. The computer memory system is then swept, allowing discrete particles to conceptually travel from surfaces to surfaces, from surfaces to volumes, from volumes to surfaces and from volumes to volumes in an abstract sense using the transport multiplier/pointer system (FIG. 7 Block 4). Any number of possible interaction models (for example, simple nuclear particle mono-energetic isotropic scatter, or multigroup, anisotropic scatter) are then employed to adjust particle interaction within volumes and make appropriate phase space adjustment to continue particle transport sweeps (FIG. 7 Blocks 4, 5 and 6). The instant invention can itself be used to create an appropriate interaction model.

By decoupling interaction from multiple collision transport, exact direct local analytic solutions along ray paths through voxels are possible. The Interaction Model then serves to produce new voxel discrete particle sources for further discrete particle transport sweeps. Thus by employing exact transport solutions of approximate discrete particles, high accuracy is achieved through the use of many phase space particles. Single multipliers are employed within the LVG, providing direct non-stochastic results very quickly.

The fundamental difference between this method and a classic Green's Function Approach [R. D. Lawrence and J. J. Doming, *A Nodal Green's Function Method for Multidimensional Diffusion Calculations*, Nuclear Science and Engineering 76, 218–231 (1980)] is that a Green's function solves a boundary value problem either over the entire time domain and all scattering interactions moments, and is therefore constrained to boundary conditions. Whether one solves a 1-D or multidimensional Green's function response, the Green's function describes all events that occur between two points over time. In the present invention, the one-dimensional first flight collision solution is a transport solution with a vacuum boundary that is irrelevant in terms of time. As a result, there is no approximation; it is a true transport solution. An outer iteration and separate interaction model account for scattering interactions and reaction rate/transient variables. The Green's function approach creates a full matrix response that includes scatter and as a result approximations such as modified diffusion theory must be made. What the present invention and Green's functions share is location coupling. However, the present invention provides far greater accuracy by separating out the scatter component in a separate time and scattering iteration.

The use of discrete particle definitions completely differentiates the present system from all prior art. Furthermore, the reduction of ray set data to form memory pointer/multiplier pairs is also unique to the instant invention, as is the use of ray sets $\Delta\mathfrak{R}$ to provide extensions for accurate LVG-to-LVG particle transport.

Explanation of the Drawings

The figures contained herein sequentially describe the invention and the manner in which it may be utilized to overcome the problems in the prior art. Set forth below is a description and explanation of each figure.

FIG. 1

This figure presents a simple depiction of a finite incremental surface traversed by a representative particle on a particular ray. Ray tracing from volumes to surfaces may deposit particles uniformly on the smallest incremental surface. Rays emanating from surfaces may be assumed to proceed from the surface center, losing some information. Alternatively, in a pre-compute variant of the instant invention, surface distribution of rays may be uniform across the surface. The angular representation of particles across rays may be explicit for all angles for each incoming ray set. Alternatively, particles from volumes to surfaces may be deposited to function coefficients constructed from a least squares error matrix to provide for surface data compression (See FIG. 6 description).

As an alternative refinement to the present invention, function coefficients may also be used to determine detailed spatial particle distributions across a single surface, sub-surface or plurality of surfaces. These methods are discussed in greater detail in the FIG. 6 description.

FIG. 2

This figure graphically illustrates the voxel and grid system concept. Voxels may be regular or irregular in shape, as depicted. Voxels may be of a homogenous material, or they may be bounded surfaces with heterogeneous sub-voxels within a larger system of grids. In the latter case, the voxel response is specified by the surface interface. A heterogeneous voxel may be generated by the present invention, and embedded into a grid system. In such a case the surface surrounding the embedded voxel acts as an interface between that voxel and the remaining grid system. Furthermore, the embedded voxel may be composed of sub-voxels with like or differing angular ray set distributions (see FIG. 6 description). When sub-voxels or a single voxel are used in such a manner, that sub-system is considered a local voxel group, LVG as defined above.

FIG. 3

This figure shows representative rays emanating from a surface point on a 2D plane. Each ray is traced with coupling multipliers associated with the source surface. The appropriate integration kernel is applied for each ray trace to accumulate surface to position multipliers in this depicted case.

FIG. 4

This figure illustrates that multiple rays with identical angle and surface state values $\Delta s$ and $\Delta \Omega$, may emanate from sub-surfaces following various paths through a system of voxels. These pathways are combined to form single multipliers from the surface to each surrounding node, though many rays may emanate from the surface. The combination of multiple rays to a single multiplier greatly improves processing time without sacrificing accuracy. Pre computation of sets of rays traversing a regular system of voxels may be used to improve processing speed in regular systems (See FIG. 7).

FIG. 5

This figure illustrates the bounding of a group of voxels to form a local voxel group. It is preferable in this 2D depiction, that the inner group of voxels is completely isolated from the outer group. In such a case, ray tracing and coupling from within the LVG terminates on the bounding surfaces, and ray tracing from outside the LVG terminates on the boundary. This isolation provides a practical mechanism for changing out individual voxels or voxel groups to arbitrary resolution. It is preferable to maintain a consistent ray set angular dependence within and without a ray-set if enough memory exists to do so. Alternatively, one may map differing angular ray-set distributions from within and without the LVG boundary. As a further refinement, one may utilize direct function coefficient deposition to provide a generalized $\Delta \Omega$ translation mechanism (described below).

FIG. 6

This figure illustrates the data relationship of the pointer/multiplier pairs and sets of the present invention. In the present invention, the pointer within the pointer/multiplier table refers to either a remote voxel interaction score terminal, a discrete surface terminal or a set of function coefficient terminals. As a preferred embodiment of the present invention, referential hash tables may be used as illustrated in this figure to reference particular ray sets with pointers on a grid position basis. There are various ways of accomplishing this particular task, and a variety of data structures may be used. Depicted in this figure is the preferable light memory footprint data structure containing ray-set indices associated with particular remote pointers. The value of this preferred embodiment is that one can quickly change out remote voxel interaction points, surfaces and functions with a minimum of processing steps when reference is made to ray-set indices.

For example, when changing out a particular position interaction point, all pointers associated with that point are identified, and all ray sets from all positions passing through that point are recomputed to affect the material property change. Use of hashing techniques as depicted, relating ray sets to terminal pointers, speeds processing of the material change out.

The pointer transport multiplier table of the present invention can be established using a ray tracing technique from particular points within voxels or surfaces of voxels. Such a ray tracing technique can take two forms, generalized with established angular sets or point to point. It may also be accomplished using a pre-computed representative ray-set scheme (see FIG. 7 detail).

In both the point to point and pre-computed cases, uniform distribution of points within voxels and surfaces are used in combination with an appropriate angle distribution $P(\Omega)$ are used to accumulate the representative ray set multipliers. Angular weights are back calculated as discussed in the description of FIG. 7 for these examples.

For the forward ray-tracing technique, from a voxel interaction point, transport multipliers are accumulated by using a number of points within each voxel representing the interactions within the voxel. Each point is given both a spatial weight, representing the volume represented by the point, and a position. Judicial selection of positions and weights is used to minimize mathematical operations associated with each point.

For each ray trace, the unique direction of the ray is ascertained and the ray is further weighted by the solid angle represented by the particular ray. In general, this is found as $w_{\Delta\Omega}=\sin(\theta)\Delta\theta\Delta\phi/4\pi$ as decomposed in polar, azimuthal spherical coordinate form where $w_{\Delta\Omega}$ represents the discrete angular weight. The problem appropriate integration kernel is applied representing attenuation through the system of voxels to further reduce the multiplier weights.

Figure 3:
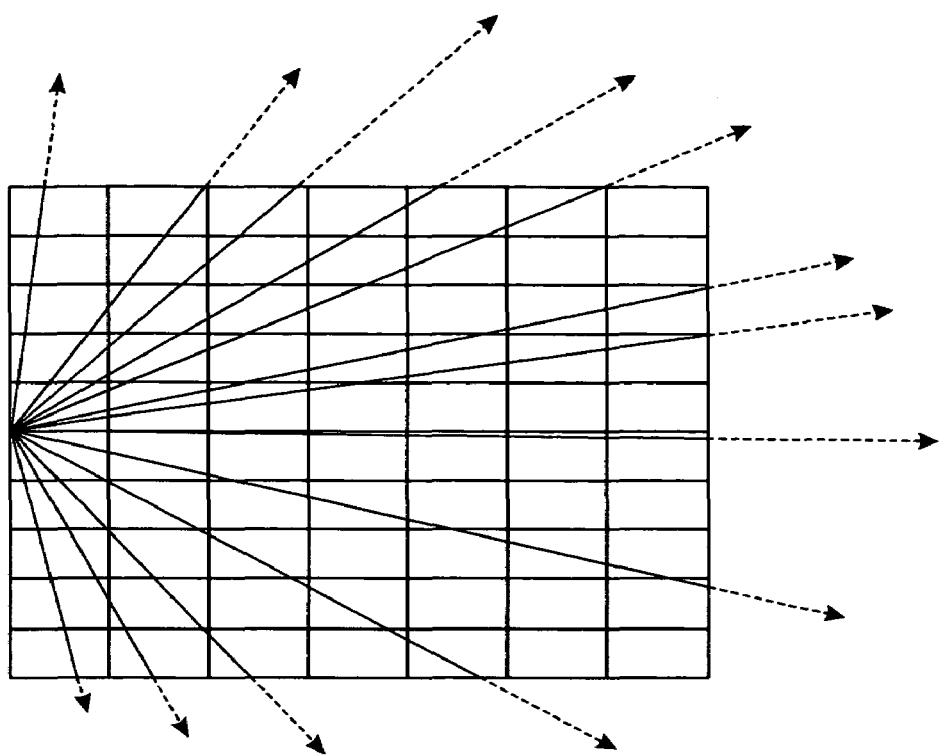
FIG. 3 depicts a subset of rays traversing a two dimensional grid system from a reference surface.
Figure 4:
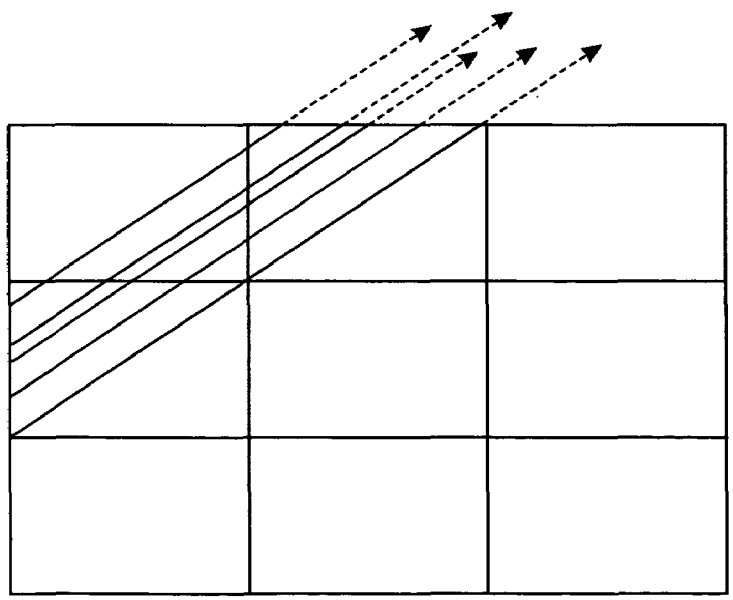
FIG. 4 represents a group of rays emanating from a surface plane of finite area and traversing a plurality of voxels wherein the group of rays occupy a solid angle group $\Delta\Omega$ within a particular ray set.
Figure 5:
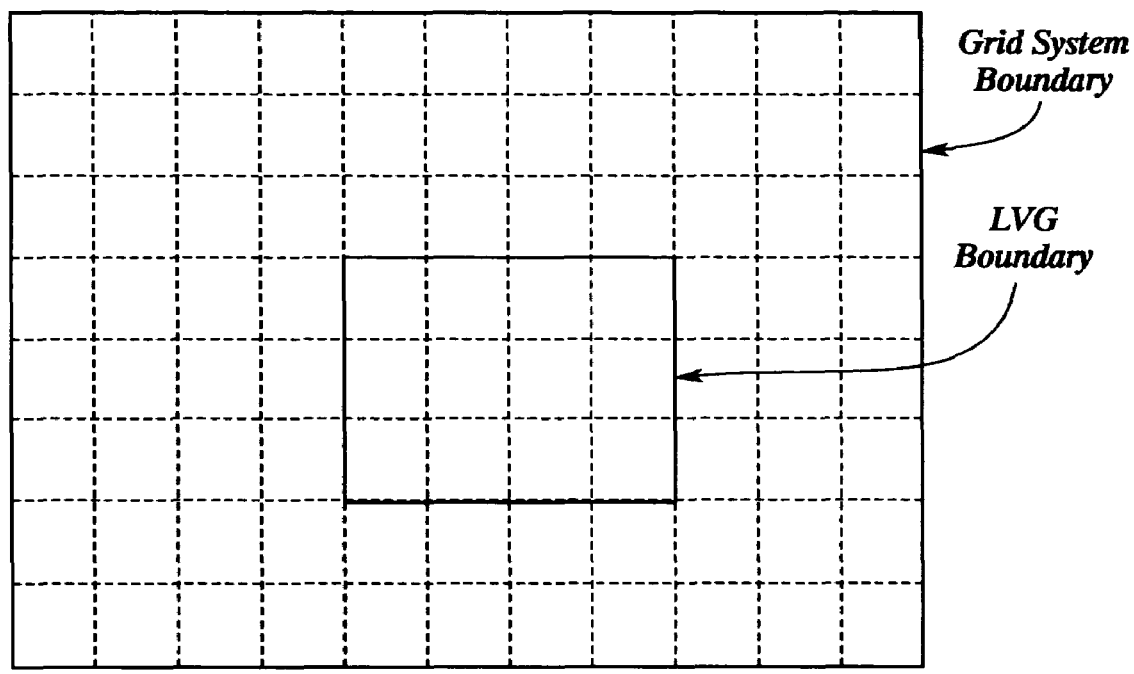
FIG. 5 depicts a reference surface within a Local Voxel Group (LVG) and contained within the grid system.

In all cases, the transport multipliers are accumulated for each representative ray or a set of representative rays (FIG. 3) tracing through the system of voxels. Weighting for both discrete surfaces and single voxel interaction points for accumulation uses the straightforward single collision integration kernel as accumulated on each ray trace pathway.

Figure 6:
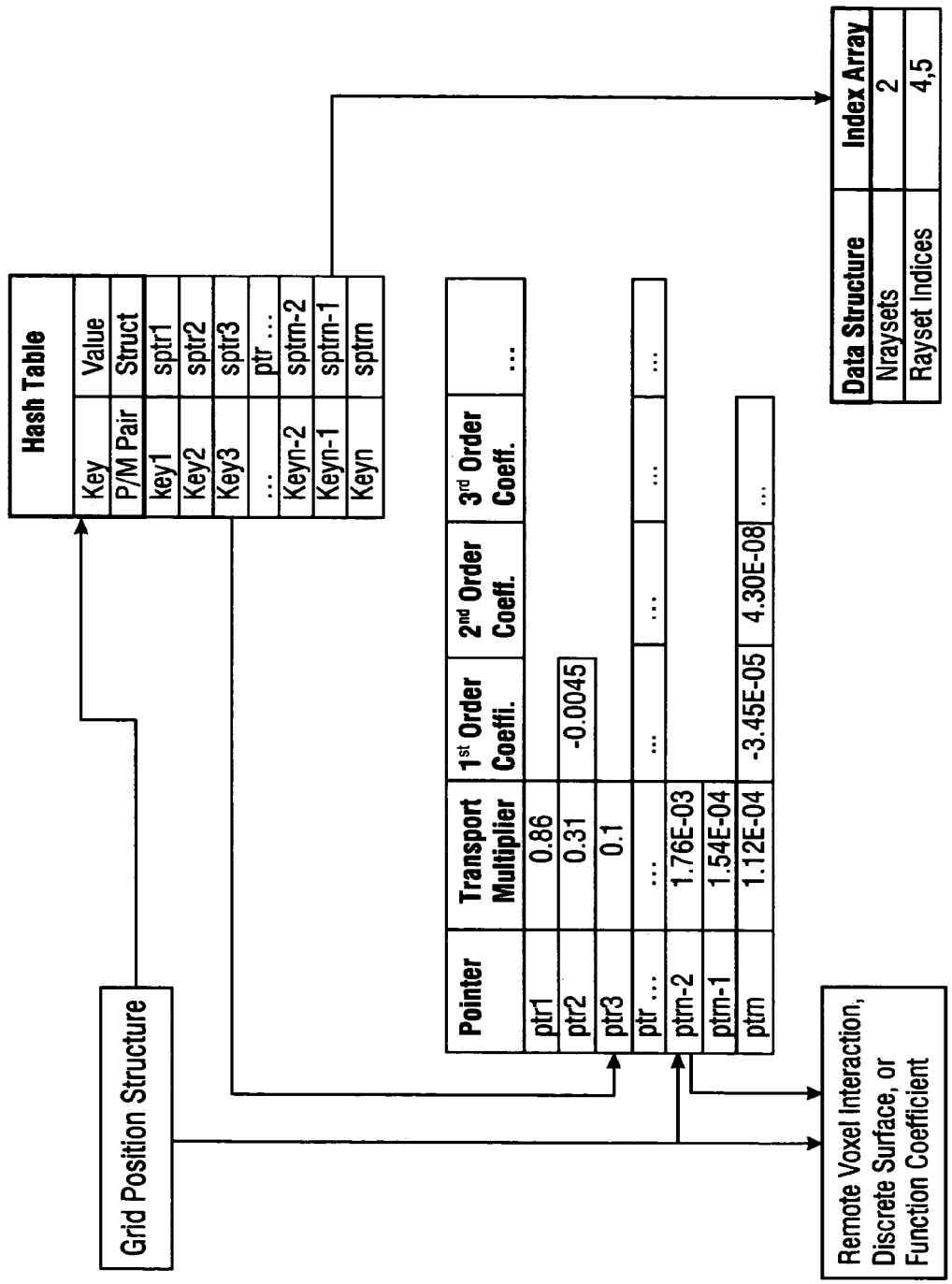
FIG. 6 depicts a data representation of the tally memory device used to store transport multipliers and pointers.

As a preferred embodiment of the present invention, the transport/multiplier system of FIG. 6 is typically generated with a hash table referring to the pointers for fast access. The multipliers are simply accumulated as a function of ray set and starting point.

The functional coefficient deposition is a preferred embodiment of the present invention that may be generated in a number of ways and has two modes of use. Each deposition to a functional coefficient is accumulated through the weighting of both the straightforward single collision integration kernel and an appropriate functional weight for each ray-set contributing to the coefficient. Function coefficient deposition may be predetermined in the pre-compute option, and the weights are generally computed only once for any given grid system.

To accumulate a functional coefficient, the preferred method is to compose a least squares error matrix which is the inverse of the curvature matrix (See P. R. Bevington, *Data Reduction and Error Analysis for the Physical Sciences*, page 153, McGraw Hill Book Company, (1969) Library of Congress Catalogue number 69-16942) associated with each ray set angle that contributes to a set of coefficients. It is well known in mathematics that given an orthogonal function, one can generate a coefficient matrix relating particular independent parameter sample points (such as indexed representative ray set direction parameters) using a least squares approach. This represents the weighting appropriate to deposit a particular sample function point to a particular coefficient. Consider for example the well-known case of a spherical harmonic basis function:

$$Y_{lm}=\{(2l+1)/4\pi(l-m)!/(l+m)!P_{lm}(\cos\theta)e^{im\phi}\}^{1/2}$$

$$Y_{l(-m)}=(-1)Y_{lm}*(\theta, \phi)$$

Where $P_{1m}(\cos\theta)$ is an associated legendre polynomial and i in the above polynomial represents an imaginary number. The construction of an angular function representing particle tallies as a function of discrete bins is $f(\theta, \phi) = \Sigma_l \Sigma_m C_{1m} \times Y_{1m}(\theta,\phi)$ where formally the summation of l is from 0 to $\infty$ and the summation of m is from −1 to +1.

As it is known before hand all possible sample point independent parameters (these are discrete ray set values of angles or direction cosines), one constructs a least squares weighting matrix by linearizing the coefficient matrix $C_{1m}$ to a convenient form $C_j$. One then constructs a coefficient weight matrix over i raysets as:

$$wij = \sum_k (y^T y)^{-1} y^T$$

where $w_{ij}$ represents the weight appropriate for each ray set direction i for j, x linearized coefficients and where $$y = \begin{vmatrix} Y_{00}1 & Y_{00}2 & Y_{00}3 \ldots & Y_{00}n \\ Y_{1(-1)}1 & Y_{1(-1)}2 & Y_{1(-1)}3 \ldots & Y_{00}n \\ \ldots & & & \\ Y_{lm}1 & Y_{lm}2 & Y_{lm}3 \ldots & Y_{lm}n \end{vmatrix}$$

$$Y_{00}i = Y_{00}(\theta_i, \phi_i)$$

with each function evaluated at each i point from 1 to n. The k summation reducing the symetric square coefficient matrix is possible because the evaluation of the function in the transport sweep is always performed at known points. The resulting weighting matrix is used to modify transport multipliers for each ray accumulated to function-coefficient pointer/transport multiplier terminals $C_j$. These linearized coefficients correspond to $C_{1m}$ so that the function $f(\theta, \phi)$ can be re-constructed with least squares fitting accuracy. The weights, $w_{ij}$ do not depend on actual values of $f(\theta, \phi)$ but rather the known sample points $\theta_i$, $\phi_i$ associated with each particular rayset contributing to n transport multipliers associated with the linearized function coefficients. The function is fully constructed in the transport problem sweep:

$$C_j = \sum_v t_v * \sum_i g_{iv} * w_{ij}$$

Where v represents each voxel contributing to a particular terminal, $g_{iv}$ is the contribution from voxel v to the tally where the coefficients are accumulated, and the summation over all relevant n angles was computed as part of the transport multiplier process in a setup calculation (FIG. 7 Block 2 or 2A). The summation over each v voxel with $t_v$ initial tally score at a voxel volume location is made during the transport sweep (FIG. 7 Block 4). Thus given a scattering or source tally at a location, and the computed transport multipliers represented by $$\sum_i g_{iv} * w_{ij},$$

the coefficients compress the operations and explicit tally angles required from n (summation over i) explicit angular sets to smaller number of coefficients (for example, there may be 4000 angles on a side for an extreme ray effect problem, but only 36 coefficients for a $P_5$ surface harmonic approximation). Or it may represent the compression from n surfaces to coefficients or other functional state values of interest.

It must be remembered that while a function is being used for data compression, it is formally a function of discrete tallies. Actual transport multipliers still proceed from surfaces using an explicit fine-grained discrete tally ray-set structure. The function only serves to translate ray set angular systems at a surface boundary, or compress data.

For the example case of a solid spherical harmonic function, the utility and first mode of use is obvious. Rather than depositing to a single interaction tally within a voxel, appropriate only for modified $P_1$ scattering the spherical harmonics function form allows for higher order anisotropic $P_n$ scattering in any given interaction voxel. It is traditional to use spherical harmonics functions of this sort for higher order scattering computation. High order double differential scattering data comes in forms that are readily amenable for use with such a representation.

The second mode of use of this embodiment is as a data compression scheme for surfaces. This alleviates the need for thousands of individual ray set accumulators on LVG surfaces to exactly represent the angular deposition distribution from voxels to surfaces. Rather than having a huge number of individually tracked i ray sets accumulate at a boundary, one only needs $C_j$ coefficients, which aggregate many different i ray set angles. In so compressing the deposition to the $C_j$ coefficients, in general fewer multiplication operations are required to construct an accurate surface shape and fewer memory locations are required to store pointer multiplier pairs.

In addition to data compression, this functional form also serves to permit translation of one set of angular sets to another set at the surface interface. An LVG surface that completely isolates an LVG or heterogeneous voxel from the general system can utilize differing angular discretization schemes. For example, one may use a point-to-point system for the outside grid system, and a ray-tracing technique or pre-computed model either inside the isolated LVG. One can also use the same system of computing discrete angles, but have differing angular sets orders. For example, one may have hundreds of ray set angles on the outside of a system, and thousands of discrete angles used in the inside of the isolated LVG. The functional forms permit translation across the boundaries through functional interpolation. In all instances, the functions are used to re-compute angular tallies over each ray set solid angle direction. One set of functional coefficients is used from the inside out, and another set from the outside in along the LVG surface boundary.

While this is one preferred form of use of the functional coefficients, this does not preclude other function deposition techniques. In the method described above, any orthogonal function may be used, and specific experiments using surface harmonics, which are related to spherical harmonics, as well as general orthogonal polynomials have been carried out.

Additionally, one may use B-Splines with pre-computed Bezier points to affect data compression and translation. Wavelets might also be employed to improve data compression accuracy (See Y. Nievergelt *Wavelets Made Easy* Birkhauser (1999) ISBN 0-8176-4061). Though generation of coefficients is different, the approach is still one of depositing transport multipliers to a coefficient system. Such a method may have advantages in reducing the coefficients associated with tally function reconstruction. However the solid spherical harmonic or surface harmonic functional forms are preferred for data consistency, historic and theoretical reasons. It is consistent with the forms used in double differential scattering cross sections allowing for simple resolution of scattering through consistent orthogonal functions.

FIG. 7

FIG. 7 presents a general flow diagram description of an algorithm for the present invention. Each process or flow block is described below.

A. Physical System Database (FIG. 7. Block 0)

Modeling of the transport of particles requires some specification of material and geometry layout associated with the transport medium. Such physical system input is usually obtained from a database.

B. Grid Construction (FIG. 7. Blocks 1–1A)

Consider for example a grid system of voxels. The grid overlays a physical system being modeled with material compositions within each voxel. Converting a graphic image of a physical system into voxels forms the grid system. Alternatively, specific input of a voxel grid system can be entered into the system (FIG. 7, 1A). Grid construction must consider variations in material composition. At the most basic level, when a single voxel encompasses multiple media, some form of homogenization must be applied. This may vary from a simple volume weighted scheme to a flux-volume weighting scheme. Such methods are well known in the art. The present invention may be used to generate a complex voxel of heterogenous sub-voxels.

For IMRT 3DRTP, the physical system is a 3D human model comprising tissue and bone as well as any metallic insert tabs and prosthesis. A grid system overlays the representation of the body and any material properties within, such as gamma ray homogenized macroscopic x-sections. This grid system may come from commercial 3D graphics package information converted to a suitable grid system. Preferably, such a grid system is irregular forming about bone and tissue to maximize accuracy by minimizing the need to homogenize voxel material.

C. Ray Set LVG Construction—Overview (FIG. 7. Blocks 2A–5)

Figure 2:
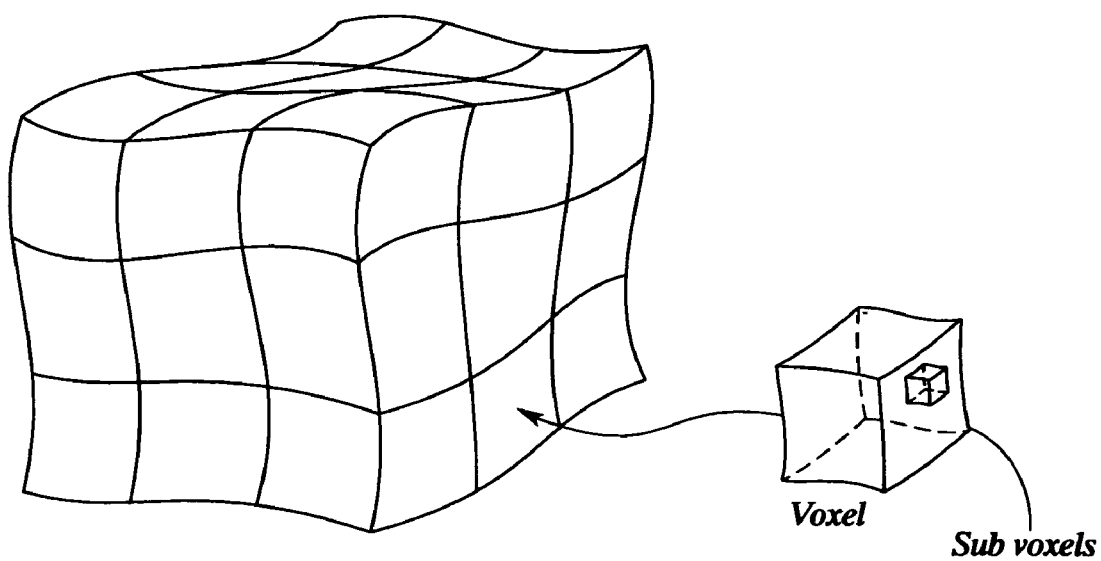
FIG. 2 is an illustrative example of the grid of the instant invention which is compiled from a $3^3$ arrangement of voxels having bent rectangular regions.

One may generate ray sets inline (FIG. 7, 2) or in a pre-constructed manner (FIG. 7, 2A and 2AI). Inline ray set/LVG construction is most appropriate for irregular grids. Pre-computed ray set geometric properties used in LVG construction are most appropriate for fast computation of regular systems. A preferred embodiment of the present invention includes all forms of ray set LVG construction as options within the computer. Pre-computed ray set geometries are preferred for analogue control systems.

Core to ray set modeling is the use of a single in-voxel interaction per interaction sweep. For each ray, the collided and un-collided particle density is used to determine the number of particles interacting, and hence subject to the Interaction Model (FIG. 7, 5), or continuing to traverse to LVG surface boundary for further particle transport (FIG. 7, 4). One may generate a ray set through a stochastic process for single collision interaction modeling (Cashwell et al., supra). One may also use direct integration of particle distributions over appropriate solid angle domains to directly compute appropriate ray set geometry factors. These factors may be analytically, semi-analytically or stochastically derived as part of a pre-computation (FIG. 7, 2AI). They are then used with the appropriate discrete angular group $\Delta\Omega$ frequencies associated with a particular representative ray, the individual length of representative ray within traversed voxels, and the appropriate single interaction particle transport kernel to compute LVG volume interaction and surface multipliers (FIG. 7, 2A).

Alternatively, one may utilize a technique similar to the discrete transfer method to determine ray sets passing through an LVG emanating from reference voxel surface or volume (Lockwood et al., supra; Cumber, supra). The major differences between such an approach within the context of the present invention is that rays emanating from volumes are not represented solely from the centroid. Most importantly, it is preferred to consider only the first flight interaction through the LVG, and use the separate interaction model to handle scattering. The present invention considers radiation transport in a forward direct approach with an iterative approach to handle particle scattering. These differences contribute to a significant improvement in accuracy. One may use a point-to-point method for surface-to-surface transport coupling that is similar to DTM, however, a pure ray tracing technique with predefined ray set angular groups provides excellent results and allows for simplified embedding of invariant voxel groups within a larger system. Furthermore, the present invention provides for direct transmission to general function coefficients with the merits of the approach as discussed in the FIG. 6 description. Finally, the present invention accumulates 1D ray set results in transport multipliers, greatly improving computational performance.

One may also use standard analytic direct solutions of appropriate particle transport equations for inline (FIG. 7, 2) computation of discrete particle LVG transport multipliers. A preferred method is to utilize stochastic methods with extremely large sample sizes for large regular polyhedron grid systems with many surfaces and overlay ray set lengths upon LVGs. For irregular grids, one preferred method is to establish a large number of points within a reference voxel volume or upon a voxel surface as centers of finite surfaces $\Delta S$ and sub-surfaces. One then computes the representative ray set with a point-to-point method.

In the point to point method, the applicable angular distribution, particularly for the IM within voxel volumes and cosine for surfaces, is factored into the associated fractions of representative rays traveling from the reference point to LVG surface point based on the solid angles formed by the set of all points from the reference voxel surface or volume.

In the forward ray-trace method, a sufficiently large number of solid angle discrete groups is used to alleviate the need for surface $P(\Omega)$ distribution assumptions.

D. Pre-Computed Ray Set (FIG. 7. Block 2AI)

For the pre-computed ray set option, the following equations describe the processes involved for computing frequency and voxel length. The frequency associated with a particle ray set over a subsurface, sub-angular group is given as:

$$f_{i,j}(\Delta S_i, \Delta\Omega_j) = \frac{\int_{\Delta S_i}\int_{\Delta\Omega_j}p(\Omega)\partial\Omega\partial S}{\int_S\int_\Omega\partial\Omega\partial S}$$

Where p(Ω) is the particle distribution appropriate for particles streaming through the applicable surface within the solid group ΔΩ$_j$. Note that different levels or collision moments of p(Ω) are possible. Near particle source distributions p(Ω) are appropriate for the Interaction Model under consideration (e.g. flat voxel volume distribution, isotropic). Relatively far from attenuated distributed sources, p(Ω) would represent a cosine distribution normal to ΔS. ΔS$_i$ and ΔΩ$_j$ represent ray set bounded surfaces and angular groups appropriate for ΔR—the applicable ray set. $f_{i,j}$(ΔS$_i$,ΔΩ$_j$) represents the indexed appropriate frequency of particles traversing a particular ray set.

We now consider an average ray length within a ray set, ΔR, within voxel I as:

$$\Delta r_{I,i,j}(\Delta S_i, \Delta \Omega_j) = \frac{\int_{\Delta S_i} \int_{\Delta \Omega_j} r_1(\Omega, S) p(\Omega) \partial \Omega \partial S}{\int_{\Delta S_i} \int_{\Delta \Omega_j} p(\Omega) \partial \Omega \partial S}$$

Where $\Delta r_{I,i,j}$(ΔS$_i$,ΔΩ$_j$) is the voxel and path dependent average ray length.

Figure 10:
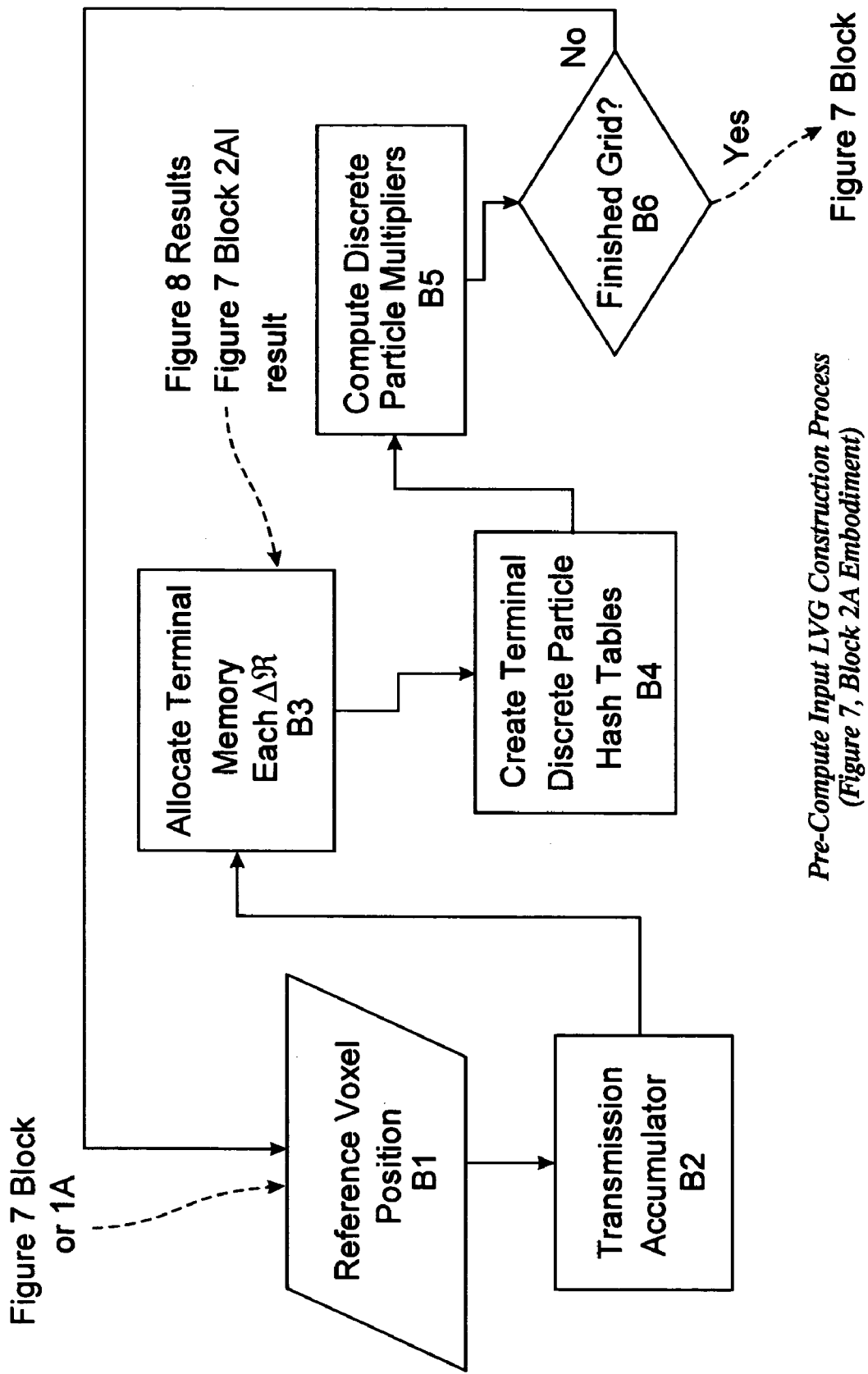
FIG. 10 illustrates an additional block body diagram sequentially depicting the steps required to determine LVG multipliers of the present invention.

The solution of these integrals, even for two-dimensional tessellations is often non-trivial. There are frequently complex dependencies between ΔS ΔΩ and ΔR. As such, the most general approach to solving pre-computed ray set frequencies and lengths is Monte Carlo. While this reverts to a stochastic process, one must remember that the computation is off-line and does not involve attenuation—hence material properties are irrelevant. The geometric properties obtained are later combined with material properties to determine transport multipliers (FIG. 10). Therefore, the results are extremely accurate as billions of particle rays can be generated without collisions and properties can be averaged to effectively solve the above integrals. The results are also generic and applicable for a particular p(Ω) with the modeled grid geometry irrespective of material.

FIG. 8

Figure 8:
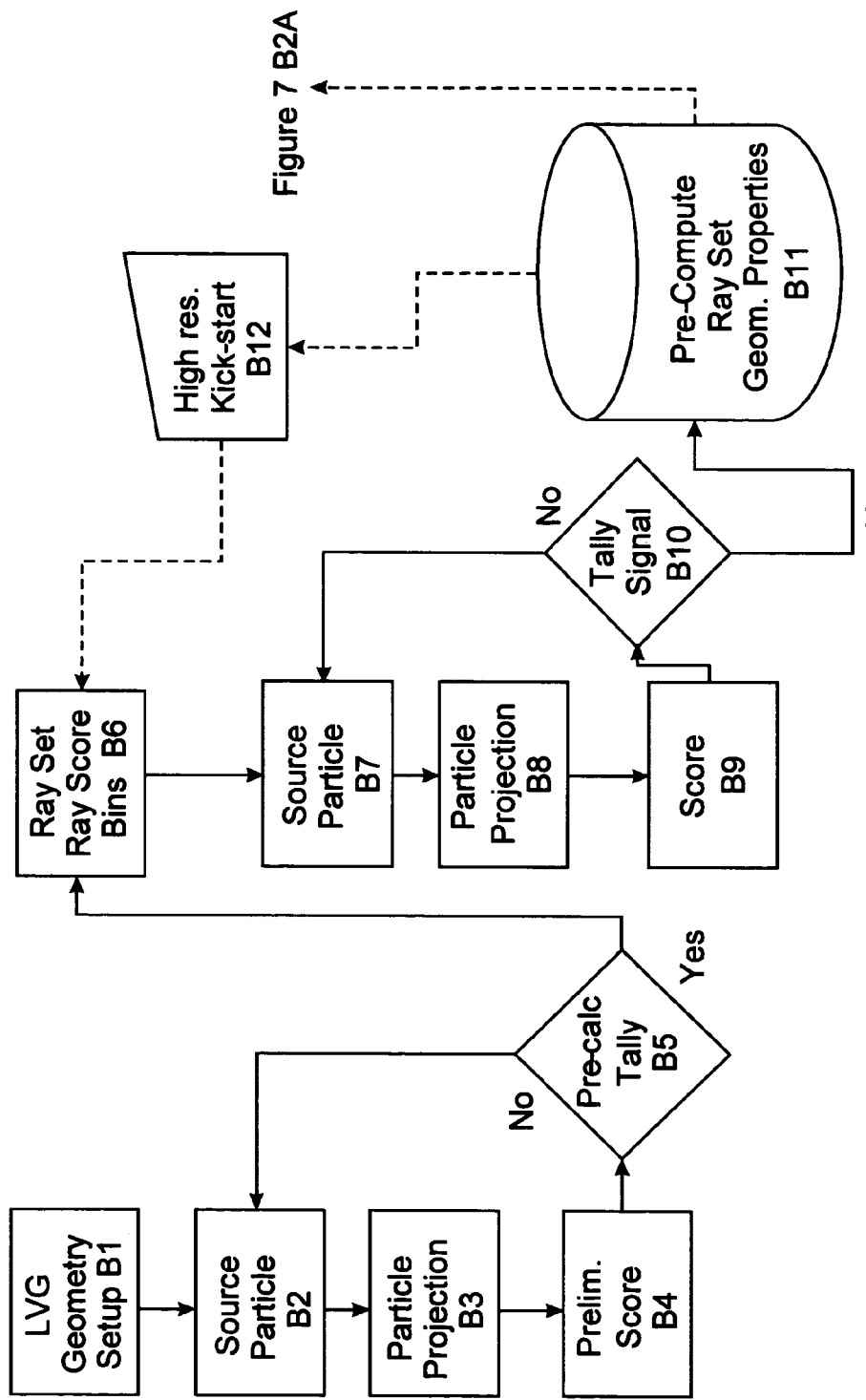
FIG. 8 depicts a block body diagram setting forth the logical steps the instant invention performs to computationally simulate ray sets of the present invention.

FIG. 8 presents a simple Monte Carlo algorithm for computing ray sets for use in the present invention as a detail of FIG. 7, Block 2AI. A geometric local voxel group is setup (FIG. 8, B1). There are no material properties associated with the voxel as only geometric properties associated with rays are being generated. A pre-calculation is carried out to determine appropriate multiple representative rays associated with particular voxel pathway ray sets (FIG. 8, B2–B5).

One generates a source particle using the p(Ω) distribution appropriate for the reference voxel surface or volume (FIG. 8, B2). Most conveniently, canonical u, v and w direction cosines are generated for Cartesian 3D coordinates. Use of local voxel volume source p(Ω) distributions are specific to each ray set library, and several distributions may be used in actual computations. Such sets represent distance moments, the first distance moment being from source (including IM source) to LVG surface boundary. The second from LVG surface to far surface and so on. Hence several outputs of FIG. 8 may be used in FIG. 7 processing.

For IMRT 3DRTP, as well as other particle transport, a preferred embodiment of the instant invention in the pre-compute mode uses a two set distribution moment approach, considering source and scattered particles from voxel volumes with their particular distribution as one set. Those particles emanating through an LVG surface are cosine distributed within angular groups ΔΩ and form the second moment set.

However, as mentioned previously in the FIG. 6 description, one can use the pre-computed set for nodes on one side of an LVG boundary, and totally different scheme, such as ray-tracing or point-to-point ray sets on the other side of a boundary. This type of an approach may be preferable when assumptions regarding p(Ω) are inadequate.

The source particle is next projected to the LVG boundary along a particular voxel pathway (FIG. 8, B3). The particle history is stored in accordance with a ray set representing the pathway and limiting path lengths are determined to appropriately develop representative rays for the ray set (FIG. 8, B4). After a pre-calculation minimum tally is achieved (FIG. 8, B5), appropriate voxel path dependent, ray set representative ray length bounds are developed (FIG. 8, B6). In a simple case, scoring bins are established based on an even bin distribution between the longest and shortest ray length in the pre-calculation. Association of ray set scores and scoring bins is most effectively accomplished by constructing a unique hash string associated with a particular particle ray set. Again, ray sets thus defined may include explicit angular groups, ΔΩ as well as values indicating projected LVG boundaries for both the local reference system and, most importantly, a surface referenced LVG adjacent system. This latter value is used for coupling LVGs at surfaces.

The source particle, particle projection and scoring procedures are repeated (FIG. 8, B7–B9), this time scoring in finer detail representative rays within ray sets developed in the preliminary calculation. If additional unique ray set pathways are found, these are scored as well without multiple rays composing the set and saved for later fine-grained ray calculations. As a practical matter, this is often the case with many angular groups and large 3D geometries, even with $10^9$ pre-calculation particle histories.

Upon receipt of a tally signal or predetermined count (FIG. 8, B10), pre-computed ray set properties are saved to a database, computer file or other storage medium (FIG. 8, B11). This particular process can be re-started for fine-grain, higher resolution calculations at a future time. This provides extremely high statistical accuracy for the geometric ray set properties (FIG. 8, B12).

FIG. 9

FIG. 9 represents output for a particular ray set of the FIG. 8 process for a flat source node emitting from a surface. This output was generated using prototype code of the present invention. Line output of FIG. 9 is described below.

Line 1: Number of Ray Sets

There can be from a few dozen to tens or even hundreds of thousands of ray sets depending upon the specification of size, angular groups and geometry. This is the 12927$^{th}$ ray set in a $6^3$, 8 angular group system. The 10 represents the number of voxels traversed. [0][0][0] represents the angular group in terms of u, v and w cosine angle groups.

Lines 2–4

Line 2 reflects the hash code used to differentiate this particular ray set. The use of hash codes (or alternatively binary trees) provides an efficient mechanism to track ray sets. The direction cosines are provided [0][0][0] followed by two entries of 336. This value represents the unique LVG exit surface point coordinate. As it happens, this value is also the same for the adjacent LVG exit surface coordinate when the local exit surface is used as a reference for an adjacent LVG system. The values that follow are pairs representing the voxel and exiting surface index, 1 thru 6 for cubic voxels (note that one may have 24, 54 or more surfaces for regular cubic voxels). Lines 3 and 4 provide the LVG surface exits for convenience.

Line 5

Line 5 represents the average path length (based on a unit 1 cubic voxel) divided by the count of particles (not used). This is followed by the longest and shortest ray within the ray set, and finally the frequency of the ray set rays as sampled from $p(\Omega)$.

Lines 6–15

Lines 6–15 provide the detailed pathway, each voxel per line of the average representative ray in [I][j][k] coordinates followed by the emergent side, followed by the average length traversed in each voxel.

Line 16

Line 16 specifies that there are 3 representative rays for the set—similar in concept to 3 panel integration.

Line 17

Line 17 provides information for the first panel, panel 0, followed by the average ray length to LVG boundary, maximum length and minimum length.

Line 18

Line 18 is a continuation of the above with the relative frequency of the representative ray within the ray set, followed by the upper length interval used.

Lines 19–28

Lines 19–28 supply the panel representative ray lengths for the pathway.

Lines 29–40 and 41–52

Lines 29–40 and 41–52 repeat the above sequence for panel 0 for the other two panels, 1 and 2 respectively. This completes the information for the 3 panel representative ray set.

While Monte Carlo is generally the preferred method for complex geometries, other methods of solving the geometric integrals presented above for ray set frequency and voxel traversal length may be employed provided that such methods are capable of providing data similar to that of FIG. 9 for the pre-compute process.

FIG. 10

Pre-Compute Material Specific LVG Construction (FIG. 7. Block 2A)

Given the output presented in FIG. 9 for average ray sets and using the material properties provided in FIG. 7, Step 1 or 1A for the general grid system, the specific LVG multipliers can be constructed. FIG. 10 presents a block diagram of this process.

The first step in processing a reference voxel position (FIG. 10, B1) is to allocate or reallocate a transmission accumulator (FIG. 10, B2). The accumulator is a function of each ray set $\Delta\Re$ as well as all explicit state particles that are affected by particle-material interaction such as energy $\Delta E$.

The next step is to allocate terminal memory for the reference voxel position (FIG. 10, B3). A terminal is defined as a pointer to a voxel LVG memory location either representing a discrete particle on the surface or an interaction tally within a voxel volume, and a transport multiplier from the reference to the terminal location. The terminals may also be functions of $\Delta\Re$ as well as other material state variables. Following this allocation, terminal discrete particle memory pointer keyed hash tables are created for accumulating multiplier values by referencing terminal positions of the LVG (FIG. 10, B4).

Finally, one walks through each ray set grid position system, starting from the reference voxel position, to compute and accumulate discrete particle multipliers from the reference to the LVG terminals (FIG. 10, B5). The hash table aids in quickly identifying the proper bin for accumulating the multiplier at a walked position. The transmission accumulator is used to tally the integration kernel transmitted values to each voxel. Applying the integration kernel to the ray set length, $\Delta r_{i,j}(\Delta S_i, \Delta\Omega_j)$, and beginning with a transmission accumulator initially set to the fraction of particles traversing the ray, $f_{i,j}(\Delta S_i, \Delta\Omega_j)$, one accumulates collision values for voxel volumes for use in the IM and transmission values for LVG surfaces. The final summation from the reference position to final position is the transport multiplier.

As an example, for a gamma ray attenuation in IMRT, a transmission multiplier at the voxel surface would be $f^*\Sigma e^{-\Delta r^*\mu}$, where the summation ($\Sigma$) is carried out for each voxel on the path to the surface. The variable f is the fraction traversing the particular ray as defined above, $\Delta r$ is each voxel path length and $\mu$ is the appropriate attenuation factor based on voxel material. There are multipliers for every material phase space state such as energy. For surface LVG points, ray sets or angular groups may be used with unique multipliers to improve accuracy. The result for each position, ray set, angular group and material state is a linear array of pointer-multiplier pairs where the pointer references an LVG particle count address in computer memory (See FIG. 6). Other storage schemes for pointer and multipliers such as two synchronized arrays are also possible. With these multipliers established, one only needs to sweep through the reference discrete particle's LVG array to transport the particle to its LVG neighbor.

In one embodiment of the instant invention, it is better from a memory utilization standpoint to simply have a vector of multipliers that are properly ordered to correspond to LVG terminal location sweeps. Instead of pointer, multiplier pairs, the multipliers are arranged in a single vector that corresponds to pointer arithmetic utilized in the sweep. This is most easily accomplished for interior LVGs that do not include boundaries.

It is important to note that the pre-computed geometric property LVG construction process does not need to be carried out at every point in the grid system. Pattern matching of material indices within the grid can be applied to identify systems where the same multipliers may be used, and simple pointer arithmetic applied to translate the LVG array values to other identical material locations. (See J. Karkkainen & E. Ukkonen, *Two-and Higher-Dimensional Pattern Matching in Optimal Expected Time*, 29 SIAM J. COMPUT., 571–589 (1999) for examples of efficient multi-dimensional pattern matching algorithms.) For regular grid systems where pre-computed LVG geometric systems are applicable, some form of pattern matching to speed up computations is preferred, as long as material compositions within the grid are not highly differentiated. Likewise, pattern matching is a preferred embodiment of the present invention for use in IMRT 3DRTP when regular grids are used.

FIG. 11

A. Inline Ray Set LVG Construction (FIG. 7. Block 2)

The preferred method for calculating discrete particle transport multipliers from reference positions in irregular grid systems throughout a single LVG is to utilize a pointto-point methodology somewhat similar to the ray layout of the discrete transfer method. The goal of the inline LVG construction is to assemble a ray set based computation of the discrete particle transport multiplier directly. As the spatial distribution of the source discrete particle is constant, and the pathway to the other discrete particle space is known, any direct conventional radiation transport method can be applied to compute the transport multiplier on a unit discrete source basis (See, e.g., Bellman et al., *An Introduction to Invariant Imbedding*, SIAM (1992); A. Shimizu, *Development of Angular Eigenvalue Method for Radiation Transport Problems*, 37 J. Nuclear Science and Technology, 15–25 (2000); Olvey et al., *Accuracy Comparisons for Variational R, T and $T^1$ Response Matrix Formulations*, 14 Annals of Nuclear Energy, 203–209 (1987); Sternick et al., *The Theory & Practice of Intensity Modulated Radiation Therapy*, Advanced Medical Publishing, 37–49 (1997)). Use of these constructions on a one-time basis necessitates the use of a large number of angular groups to mitigate ray effects. A conventional ray tracing technique can be used in such an approach, and there are times when it is necessary to do so. However, it is preferable to retain the ray set concept in preference to angular groups to link LVG surfaces even for arbitrary or irregular grid systems. Whether using the point-to-point method or conventional ray tracing, the algorithm is practically the same and is presented in FIG. 11.

The first step is to allocate memory for surfaces. For the point-to-point method, the angular distributions must be computed associated with the centers of surfaces. If one is using a ray tracing technique, the angle system is predefined. In both instances, the relative solid angle area represented by a ray is used to determine initial weighting for volume to surface coupling. Surface to surface coupling is on a per ray-set basis and does not require special weighting unless function coefficients are used as the end points. Following block B1, ray-tracing and point-to-point methods are identical.

Figure 11:
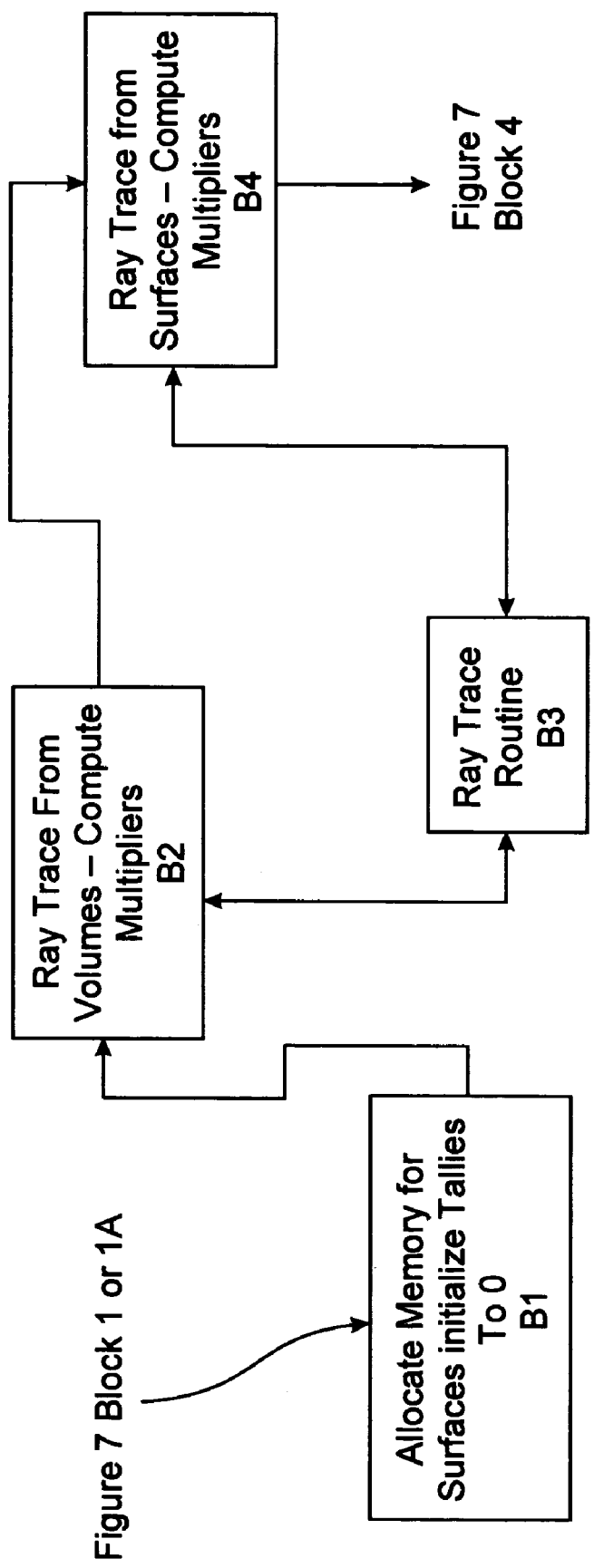
FIG. 11 Inline Ray Set Based LVG Discrete Particle Transport Multipliers, FIG. 7 Block 2 Embodiment.

In FIG. 11 Block 2, one begins by tracing rays from volumes to surfaces and accumulating point multiplier pairs. A representative ray trace routine, FIG. 11 B3 is used for this process utilizing the appropriate integration kernel. Following the coupling of volumes to surfaces, one then couples surfaces to volumes and surfaces to surface in the step represented by FIG. 11 Block 4. With surfaces, there each ray set may be individually tracked to provide fine grained detail for further transmission, and this is preferable when memory allows. When memory is constrained, one may use function coefficients to serve as surface termination points to condense data and reduce memory requirements. However, accuracy will suffer as precise angular information is lost on the boundary.

B. Initial Discrete Particle Input (FIG. 7. Block 3)

We now consider that at voxel boundaries we may have an initial condition of discrete particles specified with appropriate state variables. A discrete particle count spans the entire voxel surface from which it emanates. Coincidentally or alternatively, initial conditions can also be provided as the number of source particles emanating from voxel volumes given as a source particle count. However, these values can be converted to an initial discrete particle count on the source voxel surfaces. For IMRT 3DRTP, the initial conditions for modeling scattered radiation within tissue proceed from a primary direct ray calculation (FIG. 7, B9A). The interaction rate and possibly angular information is recorded for the first collision of the ray within voxels. This value is then used to construct an initial gamma ray discrete particle count. It is also possible to use the present invention in total with a surface discrete particle count and cosine distance moment, although it is preferable to explicitly model true rays entering a system using a representative ray approach directly. The Interaction Model of the present invention can then be used to model scattered radiation serving as a source for further particle transport. Function coefficient deposition as described in FIG. 6 may be used to handle higher order scattering interactions.

C. Discrete Particle Transport Sweep (FIG. 7. Block 4)

Once the initial source conditions have been specified for discrete particles, whether through Block 3 or 9A, one can proceed with the transport sweep. During the particle sweep, particles are transported to voxel discrete particle tallies for interaction model computation as well as LVG surface boundaries for further transport.

This comprises simply sweeping through each discrete particle location with non-zero count as a reference. At each reference, one sweeps through the linear system of LVG terminal-multiplier pairs, applying each multiplier to the reference discrete particle count to accumulate fractional particle counts at the terminal discrete particle pointer locations.

This computation may be carried out until one reaches an internal convergence where most non-interacting particles are swept from the system. Variation of the internal convergence method may be needed for transient problems where the discrete time state epoch $\Delta t$ cannot be ignored. Additionally, such a method might be preferable depending on the computation cost associated with the IM. The transport sweep, however, may be performed for reference LVGs without internal convergence. In this case, the IM is applied immediately after particles are transported to LVG boundaries. For IMRT 3DRTP, it is preferable to sweep through local LVG terminals and compute further scatters using the IM as one iterative sweep system.

FIG. 12

A. Interaction Model (FIG. 7. Block 5)

The Interaction Model receives terminal discrete particle tallies with appropriate state variables and generates new discrete particles either on voxel surfaces or from within the voxel itself, depending on model type preference. The present invention can be used to generate an Interaction Model for a relatively large voxel, which is a preferred embodiment of the system. This methodology is described below along with a simple collision probability approach to creating a valid Interaction Model. Complex collision probability methods have been employed for some time. Marleau et al. provide examples related to the use of these methods in neutron calculations (*Analytic Reductions for Transmission and Leakage Probabilities in Finite Tubes and Hexahedra*, 104 Nucl. Sci. & Eng., 209–216 (1990); *A Transport Method for Treating Three Dimensional Lattices of Heterogeneous Cells*, 101 Nucl. Sci. & Eng., 217–225 (1989)). These can be readily adapted for generalized particle transport in connection with the present invention.

One may use function coefficient deposition as previously described to create spherical harmonics functions representing the angular particle distribution. These may be used in turn with high-order double differential cross sections to compute detailed angular scatter information.

The goal of an Interaction Model is to compute the disposition of particles after a collision. This includes computation of collision parameters of the primary interacting particle after collision, changes in state, as well as generation of secondary particles with new state variables. For optics, RADAR, SONAR and radiative heat transfer, relatively simple computation of primary particle post-collision parameters is required. For nuclear radiation processes, secondary radiation such as recoil electrons from Compton scattering or additional neutrons from fission processes must be generated by the Interaction Module. For IMRT 3DRTP, gamma interactions result in photoelectric absorption and generation of photoelectrons at low γ energy. Compton Scattering with both scattered photons of reduced energy as well as recoil secondary electrons should be modeled at intermediate γ energies. For very high γ energies above 1.02 MeV, pair production processes may also be modeled.

For processes involving nuclear fission in critical systems, a special model is required that multiplies each generational infinite multiplication factor with the overall system Eigenvalue to determine local source strength. Assuming a single non-leakage parameter can be used for each voxel, this is a trivial model as is illustrated herein.

B. Simple Collision Probability Interaction Model For Radiation Particles

Figure 1:
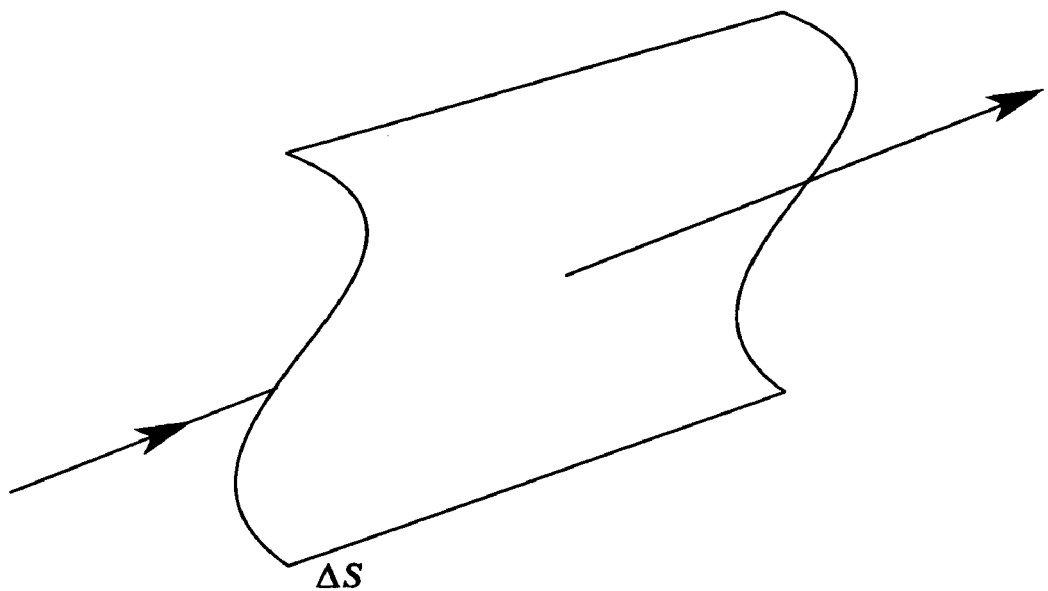
FIG. 1 illustrates a simple representation of a real single particle passing through a surface plane of finite area $\Delta s$.

As mentioned above, a simple collision parameter approach can be used for an Interaction Model. In this approach, one uses the ratios of macroscopic cross sections to determine the disposition of particles colliding within the voxel. In order to apply such a model, there should be on average less than one collision per voxel volume. For radiation transport, ideally this criteria can be met by the limiting state mean free path $1/\Sigma > d_c$, where $\Sigma$ represents the least material state total or transport macroscopic cross section and $d_c$ represents the largest possible path length across a voxel. However, practical experience has shown that such a criteria can be significantly relaxed (See FIG. 15 1Aii scattering results and description).

In this simple model, a non-leakage probability is computed and applied to all scattered and secondary particles emanating from each voxel. This probability may be obtained by assuming a flat distribution and computing the particles that exit with integration kernel attenuation. Other methods discussed in the literature can also be used.

Figure 12:
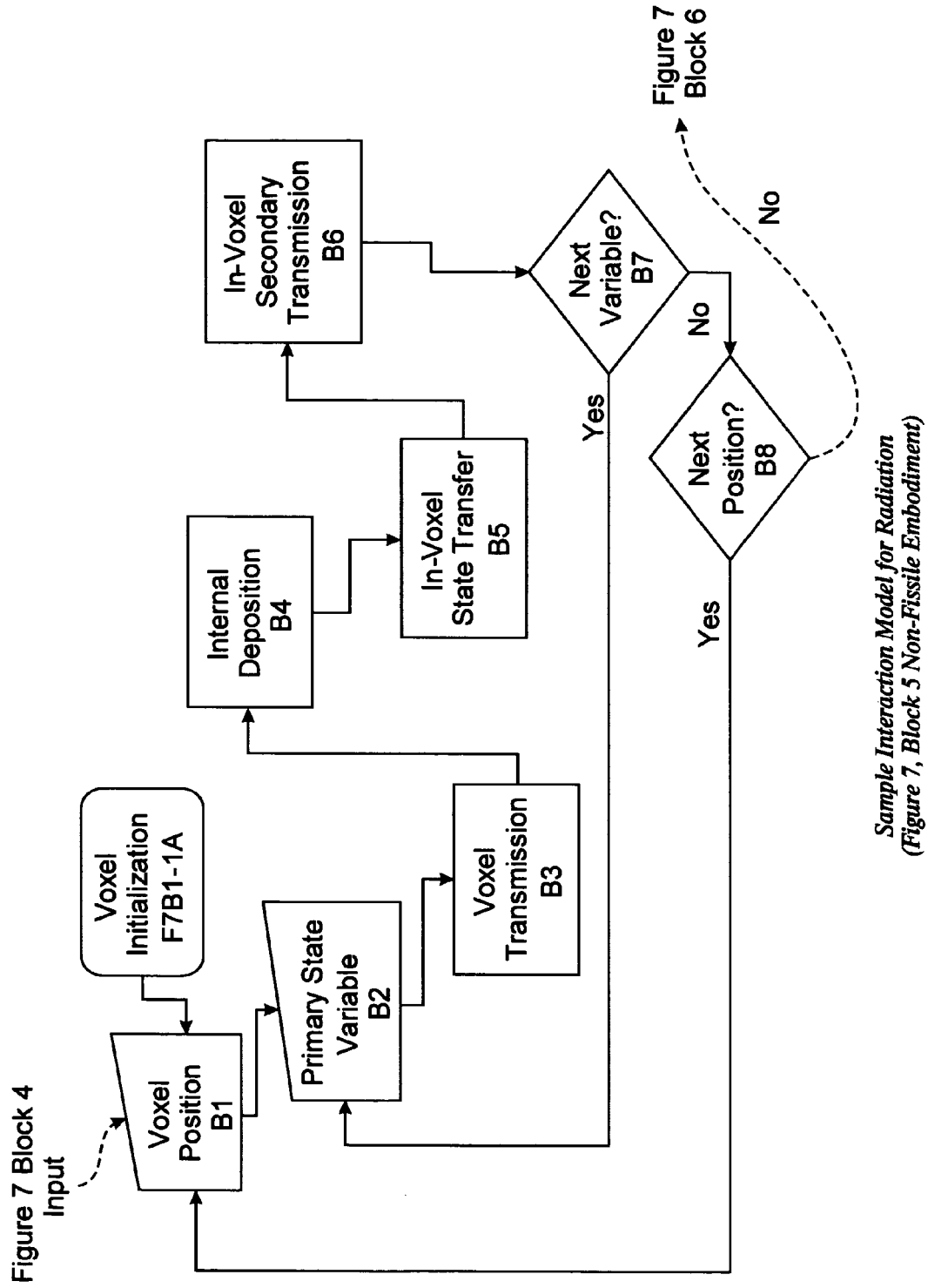
FIG. 12 through a simple flow diagram, describes the steps performed in simulating a particle within an Interactive Model.

In order to speed convergence in this model, each successive generation of interacting particles within a voxel is subject to this same non-leakage probability. FIG. 12 illustrates a simple flow diagram of such a model. Inputs to this model include those depicted in FIG. 7, Block 4 as well as possible initial condition inputs from FIG. 7, Block 9A. Grid initialization may incorporate a pre-calculation of material parameters for voxels useful for the Interaction Model. This includes non-leakage probability for each state (such as energy), particle absorption fractions, state transfer fractions and transmission fractions.

There are two approaches that one can take with regard to non-leakage and transmission. The first approach is to assume that all scattered particles appear both inwardly and outwardly directed on the voxel surface. A preferred approach is to account for further in-scatter within a voxel using the non-leakage probability, referred to as $P_{n1}$. Consider a particle that scatters from state energy group g to g' in a simple energy transfer model. We use $\Sigma r_{gg'}$ to represent the scatter/removal macroscopic cross section from group g to g' and $\Sigma t_g$ to represent the total macroscopic cross section of the voxel material. A particle that scatters (and hence has been tallied as a collision) has for its first collision a probability of $\Sigma r_{gg'}/\Sigma t_g$ of scattering to group g'. However, a particle has a probability of $\Sigma r_{gg}/\Sigma t_g$ to scatter in-group. For subsequent collisions, we have:

$\Sigma r_{gg}/\Sigma t_g * p_{n1} * \Sigma r_{gg'}/\Sigma t_g$ subsequent in-voxel scatter transfer to g' followed by, $\Sigma r_{gg}/\Sigma t_g{}^2 * p_{n1}{}^2 * \Sigma r_{gg'}/\Sigma t_g$ and so on for each subsequent generation.

It can be readily verified that as $P_{n1}$ is less than 1.0, and all transfer probabilities are less than 1.0, the total number of particles in all generations that transfer from group g to g' within such a voxel is given by:

$(\Sigma r_{gg'}/\Sigma t_g)/(1.0 - \Sigma r_{gg}/\Sigma t_g * p_{n1})$

For time Eigenvalue problems, one should multiply $p_{n1}$ by the problem Eigenvalue λ. For fission problems, group dependent infinite multiplication factor ($k_\gamma$) represents the ratio of particles produced to particles removed. It may replace or augment scatter moments as described above for sub-critical voxels. Various schemes for incorporating fission are possible.

Alternatively, one may take a scatter or fission generational approach to $p_{n1}$, such that different values of $p_{n1}$ might be appropriate for different collision moments. However the $1/\Sigma > d_c$ collision criteria should be sufficient to limit the need to use scatter transmission moments within voxel volume Interaction Models.

Proceeding with the first inline process, one establishes a voxel position (FIG. 12, B1). One then obtains a given state tally (FIG. 12, B2). Interaction tallies may be functions of all discrete particle state values as previously discussed. For each state discrete particle, interaction parameters are applied. The first voxel transmission process considers the process of scattering given a discrete particle interaction tally with state values (FIG. 12, B3). For $P_n$ scattering, the angular group of incoming rays as scored by the interaction tally is considered in the voxel discrete particle response with an appropriate scatter p(Ω). Tally entrance surface $\Delta S_i$ may also be considered when determining voxel discrete particle transmission through other discrete surfaces. However, for a preferred embodiment of the present invention, namely, use of a simple effective single collision voxel model with isotropic scatter, only the first interaction moment is treated in this detail. This is due to the complexities of multiple scatters and the relatively low statistical number of subsequent scatter.

For higher order scatter interactions, a function coefficient approach is used to determine the angular particle distribution, and this may be used to compute complex in-voxel scattering. However, such complexity is not required for most modeling tasks, it is considered better to simply use smaller voxel sizes than deal with such complex operations.

One then moves from voxel transmission to final voxel volume tallies of processes such as absorption, scatter and energy deposition (dose) as appropriate (FIG. 12, B4). Following this process, for all other states, one determines the in-voxel scatter contribution to voxel volume tallies (FIG. 12, B5). One then computes the secondary transmission of in-voxel scattered discrete particles (FIG. 12, B6). Finally, one loops through all-particle states and positions as needed to complete the IM sweep.

For 3DRTP IMRT, the above model with scatter represents a preferred, simple radiation model. However, this model can also be used in another calculation to determine larger voxel volume imbedding invariants as described herein.

C. Other Collision Probability Interaction Model For Particles

Depending on the application, one may pre-compute voxel volume interactions using various methods known in the art. However, for subsequent voxel discrete particle transmission, it is necessary to properly disposition particles leaving the voxel in appropriate ray set states when this is used as an explicit particle state value.

D. Generating an Interaction Model Based on the Present Invention

In a preferred embodiment of the present invention, the invention itself can be used to generate imbedding invariants that are used for voxel volume interaction modeling so that one is not limited to small voxels, and the criteria as defined above, namely, $1/\Sigma > d_c$ is met. As with LVG ray set properties, this operation may be performed off-line as a pre-compute, or inline after material and grid properties have been established. In either case, all that is needed is to establish an initial boundary condition on a set of voxels. For this model however, all voxels combined to create a larger voxel should be within reference LVGs.

One subdivides the grid system and solves discrete particle transport across a grid system tracking collision moment responses explicitly. Surface to volume information is retained for use in embedding the LVG into a larger system. Several surfaces may be combined to create a large voxel entrance surface as well as exit surfaces. Discrete particle density is evenly distributed across these surfaces to form the appropriate integrated voxel system response to external entrance particles. Ray tracing or point-to-point methods may be employed from the center of sub-surfaces to determine transport in the embedded system. Alternatively, a pre-compute method may also be used.

Void voxels may also be used for entrance and exit to allow for ray set initial conditions and ray set based scoring. Voids serve to provide distance moment groupings of ray sets. In such a mode, the can be used to reduce the number of explicit angular groups required for modeling within the LVG. On the input side, they serve to cause particle streaming associated with far distant moment LVG ray sets. On the output side, they are used to compute exit ray sets. Initial discrete particle groupings for all un-collapsed state groups must be explicitly modeled (See FIG. 7, Block B9A).

For problems that involve fission, explicit system responses as a function of collision time epoch must be utilized. The converged infinite system response may be determined after at least one and usually after several explicit generational responses have been determined. In no case may the group of voxels in a fissile system form a local critical system (Bellman, supra). Finally, data associated with the grouped voxels is saved for use either in later calculations as part of a pre-compute, or for use in the existing calculation.

E. Convergence (FIG. 7. Block 6)

The present invention solves particle transport as an impulsive initial value problem as opposed to a boundary value problem for non-fissile particle transport. For fissile particle transport, a generational Eigenvalue can be computed based on generational fission changes. When Eigenvalue is combined with relative reaction rate criteria, convergence to an acceptable solution can be established.

An absolute in-system particle count relative to the initial discrete particle input can be used to determine convergence, along with a computation of the ratio of residual interaction tally to total interaction tally on a voxel volume basis. Following convergence, results should be re-normalized to reflect the residual scattered or secondary IM particles that were not transported out of the system as part of the sweep. This is particularly important for problems where voxel invariant responses are being determined for incorporation into broader problem solutions.

F. Result Database Storage (FIG. 7. Block 7)

Results of calculations are preferably stored in a conventional relational or object database. Ray set data can also be stored in this manner. This is a preferred mode of storage in the instant invention.

G. Optimization/Design Engine (FIG. 7. Block 8A)

As mentioned previously, the present invention is ideal for automated design and/or treatment planning optimization. Block 8A represents a design optimization based on results of the present invention, in which the exact specification is outside of the invention.

For IMRT 3DRTP, the storage results of the instant invention are utilized, and simulated reasonable external rays are generated in order to maximize the dose to target tumors while minimizing the dose to healthy tissue. The present invention can be used to generate survey initial computations, allowing for relatively fast rejection of incident radiation that does not contribute significantly to dosing the tumor. Additionally, the present invention is ideal for modeling scattered radiation contribution to off-target healthy tissue. Commercially available optimization engines may be utilized to select the optimal beam configuration and particle intensity using the computational results of the invention.

H. Initial Particle Distribution (FIG. 7. Block 9A)

As mentioned previously, the results of an optimization engine specify an initial test particle distribution. For radiation pencil beams, the preferred modeling procedure is to model rays directly and use the Interaction Model (FIG. 7, Block 5) to determine an initial particle distribution associated with scattered radiation. Such initial radiation beams must have knowledge of the grid system. This may entail reconstruction of LVGs for certain specialty cases. Pencil beams may be modeled using representative rays. For IMRT 3DRTP, a direct ray beam calculation, using the present invention to compute scattered radiation effects, is preferable for direct radiation dose to target tissue.

FIG. 13

This figure shows the preliminary problem setup for a regular geometry utilizing the pre-compute option. The prototype used for this problem utilized FIG. 7 blocks 1A, 2A1, 2A, 3, 4, 6 and 7. Specific results for this problem setup are depicted in FIG. 14. Other prototypes demonstrated the IM aspects of the present invention in following figures.

Figure 13:
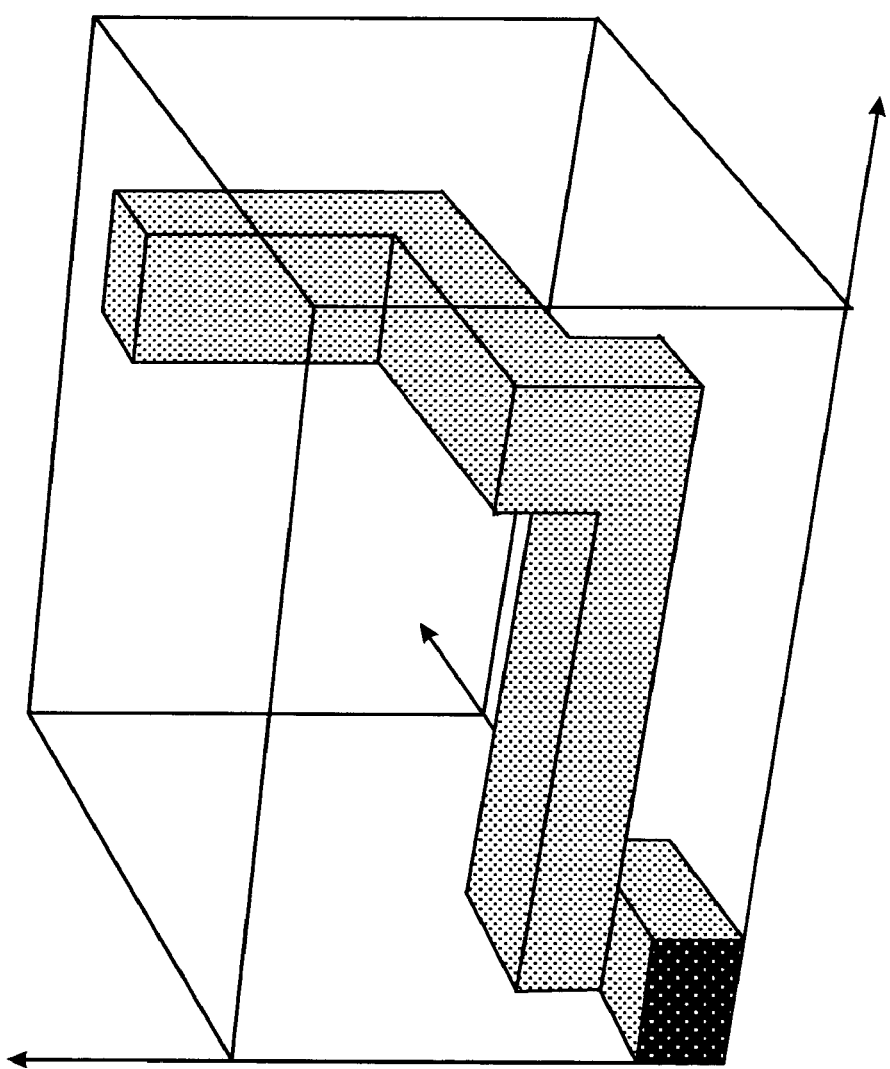
FIG. 13 depicts a sample problem layout for FIG. 14.

In the FIG. 13 preliminary problem, particles stream through the near side shaded duct entrance in an off-cosine source distribution. The specific source distribution streaming through the otherwise perfectly shielded side had a source distribution of isotropic particles uniformly distributed over a 10×10×10 $cm^3$ adjacent source voxel that of itself had no attenuation. The duct system represents has a cross section 10 cm high and wide, and extends through the 60×60×60 $cm^3$ system. Other source particles do not stream in from boundaries and scattering is not modeled in order to maximize ray effect error. Boundary conditions on all sides are a perfect vacuum. A standard total particle attenuation cross section of 0.1 $cm^{-1}$ is used and is similar to international benchmark problems, with the exception that there is no reflection of particles about three of the problem axes.

Selected results comparisons for this problem setup are presented in FIG. 14.

FIG. 14

Preliminary Planer Interaction Rate Results. This graphic depicts the results of the present invention (middle values) compared to a high particle count Monte Carlo (top values) with percent relative differences (low cell percentage values) for each $10^3$ cell. Results are presented for a plane between 40 and 50 cm above the source plane. One cell with 0.0 interactions represents the void duct while the shaded cell represents the maximum error for the plane. It is typical that direct solutions are as much as 20% to 40% off at such distances with other prior art direct methods. The signal is a few ten thousandths of the original source at these distances for an extreme ray-effect streaming problem. It should also be noted that the present invention processes multiple source distributions for this or other problems over a thousand times faster than Monte Carlo, making it ideal for design problems and 3DRTP IMRT.

The Monte Carlo code used was of the inventor's construction, and when used to compute a base case on the same computer proved to be 1000 times slower than the present invention. FIGS. 15, 16, and 17 present results against a standard international reference benchmark, using the inline ray option.

FIG. 15

FIG. 15 shows current prototype results of the present invention against a standard international benchmark problem. The prototype includes a simple interaction model, and uses variable rectangular parallelepiped voxels. It utilized an algorithm fully utilizing FIG. 7 blocks 1A, 1, 2, 4, 5, and 6.

The reference problems and result comparison has been taken from "3D Radiation Transport Benchmarks for Simple Geometries with Void Region" published in a special issue of the journal Progress in Nuclear Energy, Volume 39 Number 2 ISSN 0149-1970 (2001). The specific problem modeled from the benchmark is problem number 1.

This problem consists of a 200×200×200 cm³ on a side cube of dark absorbing material with a 100×100 ×100 cm³ central void. In the center of the void is a 20×20×20 cm³ source consisting of dark material. The problem is solved in two modes. The total macroscopic cross section for the void region is $10^{-4}$ cm$^{-1}$ while the dark absorber cross section is 0.1 cm$^{-1}$. This problem is extremely difficult for a direct method, as the material is dark, there is little or no scatter, and the problem size is large for the cross sections used.

The problem is solved in two modes. In the first mode, 1Ai, the problem both regions are pure absorbers. In the second mode, problem 1Aii, both regions have 50% scattering such that the both the absorption and scatter cross sections are 0.5×10$^{-4}$ cm$^{-1}$ and 0.05 cm$^{-1}$ respectively for both the void and dark regions. The source rate in the center block is uniformly 1 particle cm$^{-3}$-s$^{-1}$. A single referential axis is provided for comparison. The coordinate system extends from −100 cm to +100 cm for each direction.

Compared with the present invention are respected nuclear transport codes such as TORT, ARDRA and EVENT. Other codes such as PennTran did not publish exact numbers, however from the graphics provided in the journal, in all cases it appears that the present invention provides superior results. Either the exact analytic flux was used for comparison or the GVMP Monte Carlo code (a variant of MCNP). The Monte Carlo code was run for 378,000 seconds to obtain the 1Aii results presented (See FIG. 17).

As the present invention does not compute flux directly, a small node size of 2×2×2cm³ was utilized to reconstruct the flux rate. This is an additional source of error for the present invention as the node average flux is reported compared to the point fluxes computed by other codes.

For FIG. 15 scattering, the entire system was completely coupled in the present invention. The scatter problem required the modeling of fewer nodes as there was an effective vacuum boundary condition about the nodal axis. The scatter problem required full modeling of all nodes in problem 1. Node sizes were varied from the smallest 2×2× 2cm³ to 20×20×20cm³ nodes distant from the measurement axis. This was consistent with the methodologies used for the other codes. Ray tracing was used for these particular results, and this required the modeling of 9978 solid angles.

The present invention was run with the distinct setup and execution modes separate. The setup was complete such that given any source distribution, the execution time was a small fraction of the original time. FIG. 16 results present the present invention with an LVG approach breaking the reference benchmark problem in two. FIG. 17 provides machine time comparisons.

FIG. 16

This figure shows the effect of an LVG surface cut in Problem 1Ai. As this problem has no scattering, a surface is particularly problematic to model. The surface selected was at 50 cm at the void/absorber interface. Three different surface results are presented. The first surface result presents no surface cut. The second presents 4 sub-surfaces per side (an input to the prototype) with ray sets explicitly tracked through the surface. The surface cut utilized a $6^{th}$ order surface harmonics function coefficient fit per cut side. Results are shown for after the cut for the cut cases, as the results prior to the cut are identical.

With the LVG surface and only 4 sub-surfaces, adequate results were obtained. A $6^{th}$ order surface harmonic function with 57 coefficients determined using the techniques described in FIG. 6, provides good agreement as well. Additional sub-surfaces can be utilized to improve results further. The surface harmonic function was of the form:

$$f(\mu, \phi) = a_0 + \sum_m \left\{ a_m P_m(\mu) + \sum_n P_{mn}(\mu) * [b_{m,n} * \cos(n\phi) + c_{m,n} * \sin(n\phi)] \right\}$$

Where the summation of m is from 1 to 6, the summation of n is from 1 to m, $P_m(\mu)$ represents a legendre polynomial and $P_{mn}(\mu)$ an associated legendre polynomial. The cosine normal to the surface is given by $\mu$, while $\phi$ is the azimuthal angle. The coefficients, a, b and c were linearized and fit in accordance with the methodology presented in FIG. 6.

FIG. 17

This figure shows the timing results comparison for FIGS. 15 and 16. The present invention was run on an inexpensive PC processor. The clock speed of the present invention machine was higher than other cases, making timing comparisons difficult. The present invention setup time is a one-time cost for any source distribution optimization problem (such as those in 3D IMRT). As such, this computational time is used once to couple the entire system. Following this coupling, the execution times are presented and even for a tightly converged scatter problem are significantly faster than the setup time. Even the setup times for the present invention were better than those of the comparison direct methods and significantly faster than Monte Carlo.

This data, along with the FIG. 14 results indicate a 1000 fold improvement in speed through use of the present invention.

While the above-described invention has been particularly shown and described with reference to preferred embodiments thereof, it will be understood by those skilled in the art that various alterations in form and detail may be made therein and various application employed, without departing from the spirit and scope of the invention.

What is claimed is:

1. A direct computational method of algorithmically simulating the transportation of particles through a medium, comprising the steps of:
    a) establishing a set of initial particle and environmental conditions;
    b) creating a computational grid system of voxels from a physical object or system;
    c) establishing a plurality of ray sets of particle distributions with a computational algorithm;
    d) using said ray sets and appropriate integration kernel to determine invariant imbedding transport multipliers or direct collision moment transport multipliers;
    e) initiating the simulated transportation of particles by applying a plurality of discrete particle distributions within voxel interaction tallies and/or upon voxel tally surfaces;
    f) applying the transport multipliers for transporting discrete particle tallies from the first plurality of voxels to a second plurality of voxels;
    g) continuing the particle tallies in voxels as the ray sets of particle distributions sequentially transport through the grid system of voxels until a predetermined limit is attained;
    h) compiling the particle interaction tallies from within computer memory locations and applying the interaction model to determine scattering, state and accumulated interactions over a time epoch or generation;
    i) repeating steps (f–h) until inreraction reaction rates and/or the generational supercritical, critical or subcritical Eigenvalue substantially converge; and
    j) computationally producing an output indicative of the simulated particle transport.

2. A direct computational method of algorithmically simulating the transportation of particles through a medium, comprising the steps of:
    a) establishing a set of initial particle and environmental conditions;
    b) creating a computational grid system of voxels from a physical object or system;
    c) establishing a plurality of ray sets of particle distributions with a computational algorithm;
    d) using said ray sets and appropriate integration kernel to determine invariant imbedding transport multipliers or direct collision moment transport multipliers;
    e) initiating the simulated transportation of particles by applying a plurality of discrete particle distributions within voxel interaction tallies and/or upon voxel tally surfaces;
    f) applying the transport multipliers for transporting discrete particle tallies from the first plurality of voxels to a second plurality of voxels;
    g) compiling the particle interaction tallies from within computer memory locations and applying the interaction model to determine scattering, state and accumulated interactions over a time epoch or generation;
    h) repeating steps (f–g) until interaction reaction rates and/or the generational supercritical, critical or subcritical Eigenvalue substantially converge; and
    i) computationally producing an output indicative of the simulated particle transport.

3. The method of claim 1 or 2, wherein the first voxel tally location associated with a set of multipliers is zeroed prior to undertaking step (g).

4. The method of claim 1 or 2, wherein the algorithmic computation for establishing a plurality of ray sets of particle distributions is performed using Monte Carlo techniques.

5. The method of claim 1 or 2, further comprising a plurality of discrete phase space variables used to model nuclear radiation transport.

6. The method of claim 1 or 2, further comprising a plurality of discrete phase space variables used to model electromagnetic particle transport.

7. The method of claim 6, wherein said electromagnetic particle transport comprises infrared waves, optical waves, UV waves, or radio waves.

8. The method of claim 1 or 2, further comprising a plurality of discrete phase space variables used to model radiative heat transfer.

9. A direct computational method of algorithmically simulating the transportation of particles through a mediums comprising:
    (a) pre-processing a plurality of ray sets of particle distributions with a computational algorithm;
    (b) using said ray sets and appropriate integration kernel to determine invariant imbedding transport multipliers or direct collision moment transport multipliers;
    (c) applying the transport multipliers for transporting discrete particle tallies from a first plurality of voxels to a second plurality of voxels using an iterative process;
    (d) compiling the particle interaction tallies from Within Computer memory locations and applying the interaction model to determine interactions over a time epoch or generation; and
    (e) computationally producing an output indicative of the simulated particle transport.

10. A direct computational method of algorithmically simulating the transportation of particles through a medium, comprising:
    (a) preprocessing a plurality of ray sets of particle distributions with a computational algorithm;
    (b) using said ray sets and appropriate integration kernel to determine invariant imbedding transport multipliers or direct collision moment transport multipliers;
    (c) initiating the simulated transportation of particles by applying a plurality of discrete particle distributions within voxel interaction tallies and/or upon voxel tally surfaces using an iterative process;
    (d) compiling the particle interaction tallies from within computer memory locations and applying the interaction model to determine interactions over a time epoch or generation; and
    (e) computationally producing an output indicative of the simulated particle transport.

11. The method of claim 9, wherein the first voxel tally location associated with a set of multipliers is zeroed prior to undertaking step (d).

12. The method of claim 9 or 10, further comprising a plurality of discrete phase space variables used to model nuclear radiation transport.

13. The method of claim 9 or 10, further comprising a plurality of discrete phase space variables used to model electromagnetic particle transport.

14. The method of claim 13, wherein said electromagnetic particle transport comprises infrared waves, optical waves, UV waves, or radio waves.

15. The method of claim 9 or 10, further comprising a plurality of discrete phase space variables used to model radiative heat transfer.

* * * * *